United States Patent
Troudt et al.

(10) Patent No.: US 12,369,815 B2
(45) Date of Patent: Jul. 29, 2025

(54) ALDEHYDE AND KETONE RECEPTOR MODIFICATION OF GRAPHENE

(71) Applicant: REGENTS OF THE UNIVERSITY OF MINNESOTA, Minneapolis, MN (US)

(72) Inventors: Blair K. Troudt, St. Paul, MN (US); Philippe Pierre Joseph Buhlmann, Minneapolis, MN (US); Steven Koester, Edina, MN (US); Xue Zhen, Plymouth Meeting, PA (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 814 days.

(21) Appl. No.: 17/689,760

(22) Filed: Mar. 8, 2022

(65) Prior Publication Data
US 2022/0304589 A1 Sep. 29, 2022

Related U.S. Application Data

(60) Provisional application No. 63/161,640, filed on Mar. 16, 2021.

(51) Int. Cl.
*A61B 5/08* (2006.01)
*A61B 5/05* (2021.01)
(Continued)

(52) U.S. Cl.
CPC .............. *A61B 5/082* (2013.01); *A61B 5/05* (2013.01); *B05D 1/007* (2013.01); *C01B 32/194* (2017.08);
(Continued)

(58) Field of Classification Search
None
See application file for complete search history.

(56) References Cited

U.S. PATENT DOCUMENTS 8,294,135 B2 10/2012 Lebedev et al.
8,581,262 B2 11/2013 Pan et al.
(Continued)

FOREIGN PATENT DOCUMENTS

AU 2019224011 11/2021
AU 2019260666 11/2021
(Continued)

OTHER PUBLICATIONS

"Final Office Action," for U.S. Appl. No. 17/387,503 mailed Nov. 4, 2024 (20 pages).
(Continued)

*Primary Examiner* — Xiaoyun R Xu
(74) *Attorney, Agent, or Firm* — Pauly, DeVries Smith & Deffner LLC

(57) ABSTRACT

Embodiments herein relate to chemical sensors based on the non-covalent surface modification of graphene with compounds containing hydrazine or hydroxylamine functional groups for the detection of aldehyde and ketone-bearing analytes. In an embodiment, a medical device is included having a graphene varactor included a graphene layer and a self-assembled monolayer disposed on an outer surface of the graphene layer through electrostatic interactions between a partial positive charge on hydrogen atoms of one or more hydrocarbons of the self-assembled monolayer and a π-electron system of graphene. The self-assembled monolayer can include one or more compounds having one or more hydrazine groups or hydroxylamine groups, substituted hydrazine or hydroxylamine groups, or derivatives thereof. Other embodiments are also included herein.

20 Claims, 14 Drawing Sheets

(51) Int. Cl.
  *B05D 1/00* (2006.01)
  *C01B 32/194* (2017.01)
  *G01N 27/22* (2006.01)

(52) U.S. Cl.
  CPC ........ *G01N 27/22* (2013.01); *A61B 2562/125* (2013.01); *C01B 2204/22* (2013.01); *G01N 2027/222* (2013.01)

(56) References Cited

U.S. PATENT DOCUMENTS

| | | |
|---|---|---|
| 8,951,473 B2 | 2/2015 | Wang et al. |
| 8,961,830 B2 | 2/2015 | Reynolds et al. |
| 9,011,779 B1 | 4/2015 | Anglin, Jr. et al. |
| 9,085,715 B2 | 7/2015 | Berthelot et al. |
| 9,267,908 B2 | 2/2016 | Wang et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,620,727 B2 | 4/2017 | Laaksonen et al. |
| 9,671,392 B2 | 6/2017 | Jeppsen et al. |
| 9,689,836 B2 | 6/2017 | Makaram et al. |
| 9,775,241 B2 | 9/2017 | Walczak et al. |
| 9,859,034 B2 | 1/2018 | Sjong |
| 11,079,371 B2 | 8/2021 | Zhen et al. |
| 11,156,576 B2 | 10/2021 | Harada et al. |
| 11,293,914 B2 | 4/2022 | Zhen et al. |
| 11,867,596 B2 | 1/2024 | Zhen et al. |
| 11,923,419 B2 | 3/2024 | Zhen et al. |
| 2009/0104435 A1 | 4/2009 | Hutchison et al. |
| 2012/0058350 A1 | 3/2012 | Long et al. |
| 2012/0184041 A1 | 7/2012 | Carella et al. |
| 2012/0214172 A1 | 8/2012 | Chen et al. |
| 2014/0145735 A1 | 5/2014 | Koester et al. |
| 2015/0298115 A1 | 10/2015 | Campidelli et al. |
| 2015/0338390 A1 | 11/2015 | Anglin et al. |
| 2016/0093806 A1 | 3/2016 | Turchanin |
| 2016/0289769 A1 | 10/2016 | Schwartz et al. |
| 2016/0334386 A1 | 11/2016 | Anglin, Jr. et al. |
| 2016/0356741 A1 | 12/2016 | Makaram et al. |
| 2017/0212116 A1 | 7/2017 | Braga et al. |
| 2017/0296979 A1 | 10/2017 | Swett et al. |
| 2017/0307576 A1 | 10/2017 | Anglin, Jr. et al. |
| 2018/0110444 A1 | 4/2018 | Sherwood et al. |
| 2019/0025237 A1 | 1/2019 | Kelly et al. |
| 2019/0257825 A1 | 8/2019 | Zhen et al. |
| 2019/0331661 A1 | 10/2019 | Zhen et al. |
| 2020/0166435 A1 | 5/2020 | Sherwood et al. |
| 2020/0191737 A1 | 6/2020 | Sherwood et al. |
| 2021/0057526 A1 | 2/2021 | Zhen et al. |
| 2021/0072208 A1 | 3/2021 | Sherwood et al. |
| 2021/0242685 A1 | 8/2021 | Godridge et al. |
| 2021/0356457 A1 | 11/2021 | Zhen et al. |
| 2021/0369250 A1 | 12/2021 | Buhlmann et al. |
| 2022/0291198 A1 | 9/2022 | Zhen et al. |
| 2024/0290841 A1 | 8/2024 | Zhen et al. |

FOREIGN PATENT DOCUMENTS

| | | |
|---|---|---|
| CA | 2673142 | 4/2008 |
| CA | 2800887 | 12/2011 |
| CN | 102183557 | 9/2011 |
| CN | 103341350 W | 10/2013 |
| CN | 103926278 W | 7/2014 |
| CN | 103950920 | 7/2014 |
| CN | 104730121 W | 6/2015 |
| CN | 103852505 | 11/2015 |
| CN | 105021680 W | 11/2015 |
| CN | 103877574 | 1/2016 |
| CN | 105688995 | 6/2016 |
| CN | 107180706 | 9/2017 |
| CN | 109206628 W | 1/2019 |
| CN | 109422835 W | 3/2019 |
| CN | 111788477 | 10/2020 |
| CN | 112041672 | 12/2020 |
| CN | 114364311 | 4/2022 |
| CN | 117083519 W | 11/2023 |
| EP | 3431977 | 1/2019 |
| EP | 3755995 | 12/2020 |
| EP | 3785025 | 3/2021 |
| IN | 201627028955 | 10/2016 |
| JP | H0682455 | 3/1994 |
| JP | 2012122814 | 6/2012 |
| JP | 5837058 | 11/2015 |
| JP | 20190204415 | 2/2019 |
| JP | 2020041981 W | 3/2020 |
| JP | 2021514478 | 6/2021 |
| JP | 2021520501 | 8/2021 |
| KR | 20130133373 W | 12/2013 |
| KR | 20170057001 | 5/2017 |
| KR | 101797737 | 11/2017 |
| WO | 2010097518 | 9/2010 |
| WO | 2011158068 | 12/2011 |
| WO | 2012135565 | 10/2012 |
| WO | 2012138632 | 10/2012 |
| WO | 2015179623 | 11/2015 |
| WO | 2016145300 | 9/2016 |
| WO | 2017066583 | 4/2017 |
| WO | 2017095922 | 6/2017 |
| WO | 2019164922 | 8/2019 |
| WO | 2019209918 | 10/2019 |
| WO | 2021034844 | 2/2021 |
| WO | 2021242685 | 12/2021 |
| WO | 2022197521 | 9/2022 |

OTHER PUBLICATIONS

"Response to Final Rejection," mailed on Nov. 4, 2024, for U.S. Appl. No. 17/387,503, submitted via Patent Center on Jan. 28, 2025, 10 pages.

Keithley Instruments "Model 4200-SCS Semiconductor Characterization System User's Manual," KTE Interactive Version 9.1 SP2, Feb. 2017, p. 1-335. (Year: 2017).

Saxena, Swasti, et al."Metal-tetraphenylporphyrin functionalized carbon nanotube composites as sensor for benzene, toluene and xylene vapors.," Adv. Mater. Lett 5.8 (2014): 472-478. (Year: 2014).

"Determination of Carbonyl Compounds By High performance Liquid Chromatography (HPLC)," EPA Method 8315A 1996 (34 pages).

File History for U.S. Appl. No. 16/280,635 downloaded Apr. 22, 2022 (373 pages).

File History for U.S. Appl. No. 16/393,177 downloaded Apr. 22, 2022 (452 pages).

"First Examination Report," for Australian Patent Application No. 2019224011 mailed Apr. 9, 2021 (4 pages).

"First Examination Report," for Australian Patent Application No. 2019260666 mailed Oct. 13, 2021 (4 pages).

"International Preliminary Report on Patentability," for PCT Application No. PCT/US2019/018741 mailed Sep. 3, 2020 (11 pages).

"International Preliminary Report on Patentability," for PCT Application No. PCT/US2019/028870 mailed Nov. 5, 2020 (11 pages).

"International Preliminary Report on Patentability," for PCT Application No. PCT/US2020/046829 mailed Mar. 3, 2022 (9 pages).

"International Search Report and Written Opinion," for PCT Application No. PCT/US2019/018741 (our file 115.0320WOU1) mailed May 6, 2019 (17 pages).

"International Search Report and Written Opinion," for PCT Application No. PCT/US2019/028870 (our file 115.0325WOU1) mailed Aug. 20, 2019 (17 pages).

"International Search Report and Written Opinion," for PCT Application No. PCT/US2020/046829 (our file 115.0372WOU1) mailed Nov. 18, 2020 (15 pages).

"International Search Report and Written Opinion," for PCT Application No. PCT/US2021/033872 (our file 115.0383WOU1) mailed Sep. 13, 2021 (14 pages).

"Office Action," for Japanese Patent Application No. 2020-558952 (our file 115.0325JPWO) mailed Dec. 7, 2021 (6 pages) with English Translation.

(56) References Cited

OTHER PUBLICATIONS

"Office Action," for Japanese Patent Application No. 2020-566542 (our file 115.0320JPWO) mailed Aug. 24, 2021 (9 pages) with English Translation.
"Response to Communication Pursuant to Rules 161(1) and 162 EPC," for European Patent Application No. 19709268.7 (our file 115.0320EPWO) filed Apr. 1, 2021 (12 pages).
"Response to Communication Pursuant to Rules 161(1) and 162 EPC," for European Patent Application No. 19733177.0 (our file 115.0325EPWO) filed Jun. 4, 2021 (20 pages).
"Response to Examination Report," for Australian Patent Application No. 2019224011 (our file 115.0320AUWO) filed Jul. 23, 2021 (22 pages).
"Response to Examination Report," for Australian Patent Application No. 2019260666 (our file 115.0325AUWO) filed Oct. 29, 2021 (20 pages).
Allen, Matthew J., et al. "Honeycomb Carbon: A Review of Graphene," Chem. Rev. 2010, 110, 132-145 (14 pages).
An, Xiaohong, et al. "Stable Aqueous Dispersions of Noncovalently Functionalized Graphene from Graphite and their Multifunctional High-Performance Applications," Nano Lett. 2010, 10, 4295-4301 (7 pages).
Bair, Kenneth W., et al. "(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J., et al. "Electrochemical Methods: Fundamentals and Applications," Wiley New York: 1980; vol. 2 (850 pages).
Biedermann, Frank, et al. "Experimental Binding Energies in Supramolecular Complexes," Chem. Rev. 2016, 116(9), 5216-5300 (85 pages).
Bock, Harald, et al. "Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Brust, Mathias, et al. "Novel Gold-Dithiol Nano-Networks with Non-Metallic Electronic Properties," Adv. Mater. 1995, 7, No. 9 795-797 (3 pages).
Brust, Mathias, et al. "Synthesis of Thiol-derivatised Gold Nanoparticles in a Two-phase Liquid-Liquid System," J. Chem. Soc., Chem. Commun., 1994, 801-802 (2 pages).
Cancilla, Devon A., et al. "O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).
Cao, Mengmei, et al. "Electrochemical and Theoretical Study of $\pi$-$\pi$ stacking Interactions between Graphitic Surfaces and Pyrene Derivatives," J. Phys. Chem. C 2014, 118(5), 2650-2659 (10 pages).
Capuano, Rosamaria, et al. "Corroles-Porphyrins: A Teamwork for Gas Sensor Arrays," Sensors, 2015, vol. 15, pp. 8121-8130 (10 pages).
Chamberlain II, Richard V., et al. "Electrostatically-induced Inclusion of Anions in Cyclodextrin Monolayers on Electrodes," Langmuir 2000, 1388-1396 (9 pages).
Cheng, Zengguang, et al. "Suspended Graphene Sensors with Improved Signal and Reduced Noise," Nano Lett. 2010, 10, 1864-1868 (5 pages).
Chung, Po-Ren, et al. "Formaldehyde Gas Sensors: A Review," Sensors 2013, 13, 4468-4484 (17 pages).
Connors, Kenneth A., et al. "The Stability of Cyclodextrin Complexes in Solution," Chem. Rev. 1997, 97, 1325-1357 (34 pages).
Deen, David A., et al. "Graphene-Based Quantum Capacitance Wireless Vapor Sensors," IEEE Sensors Journal, vol. 14, No. 5, May 2014, pp. 1459-1466 (8 pages).
Di Natale, Corrado, et al. "Lung Cancer Identification by the Analysis of Breath by Means of an Array of Non-Selective Gas Sensors," Biosensors and Bioelectronics 18 (2003) 1209-1218 (10 pages).

Ebrish, M. A., et al. "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A., et al. "Effect of Noncovalent Basal Plane Functionalization of the Quantum Capacitance in Graphene," ACS Appl. Mater. Interfaces 2014, 6, 10296-10303 (8 pages).
Elemans, Johannes A.A.W., et al. "Molecular Materials by Self-Assembly of Porphyrins, Phthalocyanines, and Perylenes," Adv. Mater. 2006, 18, 1251-1266 (16 pages).
Fogel, Yulia, et al. "Graphitic Nanoribbons with Dibenzo[e,l]pyrene Repeat Units: Synthesis and Self-Assembly," Macromolecules 2009, 42, 6878-6884 (7 pages).
Fuchs, Patricia, et al."Breath gas aldehydes as biomarkers of lung cancer," Int. J. Cancer 2010, 126 (11), 2663-70 (8 pages).
Gautam, Madhav, et al. "Gas sensing properties of graphene synthesized by chemical vapor deposition," Materials and Science Engineering C31 (2011) 1405-1411 (7 pages).
Georgakilas, Vasilios, et al. "Functionalization of Graphene: Covalent and Non-Covalent Approaches, Derivatives and Applications," Chem. Rev. 2012, 112(11), 6156-6214 (59 pages).
Georgakilas, Vasilios, et al. "Noncovalent Functionalization of Graphene and Graphene Oxide for Energy Materials, Biosensing, Catalytic, and Biomedical Applications," Chem. Rev. 2016, 116, 5464-5519 (56 pages).
Ghosh, Sujoy, et al. "Effect of 1-Pyrene Carboxylic-Acid Functionalization of Graphene on Its Capacitive Energy Storage," J. Phys. Chem. C 2012, 116, 20688-20693 (6 pages).
Giancane, Gabriele, et al. "State of Art in Porphyrin Langmuir-Blodgett Films as Chemical Sensors," Advances in Colloid and Interface Science, 2012, vol. 171-172, pp. 17-35 (Year: 2012), 19 pages.
Good, Robert J. "Contact angle, wetting, and adhesion: a critical review," J. Adhesion Sci. Technol. 1992, vol. 6, No. 12, pp. 1269-1302 (34 pages).
Gorodetsky, Alon A., et al. "Electrochemistry Using Self-assembled DNA Monolayers on Highly Oriented Pyrolytic Graphite," Langmuir 2006, 22, 7917-7922 (6 pages).
Guo, Yujing, et al. "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Guo, Zanru, et al. "Light-Switchable Single-Walled Carbon Nanotubes Based on Host-Guest Chemistry," Adv. Funct. Mater. 2013, 23, 5010-5018 (18 pages).
Hasobe, Taku "Photo- and Electro-Functional Self-Assembled Architectures of Porphyrins," Physics Chemistry Chemical Physics, 2012, 14, pp. 15975-15987 (Year: 2012), 13 pages.
Hill, Ernie W., et al. "Graphene Sensors," IEEE Sensors Journal, vol. 11, No. 12, Dec. 2011 (10 pages).
Hinnemo, Malkolm, et al. "On Monolayer Formation of Pyrenebutyric Acid on Graphene," Langmuir, 2017, vol. 33, No. 14 pp. 3588-3593 (6 pages).
Hong Chan, Wing, et al. "Optodes based on a calixarene ester for the determination of aldehydes via in situ generation of the Girard's reagent P derivative," Analyst 1998, 123 (12), 2851-2856 (6 pages).
Hoshika, Yasuyuki, et al "Sensitive gas chromatrographic determination of lower aliphatic carbonyl compounds as their pentafluorophenylhydrazones," Journal of Chromatography, 152 (1978) 224-227 (4 pages).
Hsiao, Min-Chien, et al. "Preparation and properties of a graphene reinforced nanocomposite conducting plate," J. Mater. Chem., 2010, 20, 8496-8505 (10 pages).
Hsieh, Chien-Te, et al. "Field emission from various CuO nanostructures," Applied Physics Letters 2003, vol. 83, No. 6 (3 pages).
Huang, Ke-Jing, et al. "Novel electrochemical sensor based on functionalized graphene for simultaneous determination of adenine and guanine in DNA," Colloids and Surfaces B: Biointerfaces 82 (2011) 543-549 (7 pages).
Hunter, Christopher A., et al. "The Nature of IT-TT Interactions," J. Am. Chem. Soc. 1990, 112, 5525-5534 (10 pages).

(56) References Cited

OTHER PUBLICATIONS

Tezhokin, I., et al. "Porphyrin molecules boost the sensitivity of epitaxial graphene for NH3 detection," J. Phy .: Condens. Matter 29 (2017) (11 pages).
Jiao, Dezhi, et al. "Supramolecular Peptide Amphiphile Vesicles through Host- Guest Complexation," Angew. Chem. Int. Ed. 2012, 51, 9633-9637 (5 pages).
Josef, Szejtli "Introduction and General Overview of Cyclodextrin Chemistry," Chem. Rev. 1998, 98, 1743-1753 (12 pages).
Kang, Xinhuang, et al. "Glucose Oxidase-graphene-chitosan modified electrode for direct electrochemistry and glucose sensing," Biosensors and Bioelectronics 25 (2009) 901-905 (5 pages).
Knipp, Ralph J., et al. "A versatile probe for chemoselective capture and analysis of carbonyl compounds in exhaled breath," Anal Methods, 2015, 7, 6027 (7 pages).
Kobayashi, Keiko, et al. "Gas chromatrographic determination of low-molecular- weight carbonyl compounds in aqueous solution as their O-(2,3,4,5,6- pentafluorobenzyl) oximes," Journal of Chromatography A 1980, 187(2), 413-417 (5 pages).
Koester, Steven J. "High Quality Factor Graphene Varactors for Wireless Sensing Applications," Applied Physics Letters 99, 163105 (2011), 3 pages.
Kozbial, Andrew, et al. "Study on the surface energy of graphene by contact angle measurement," Langmuir 2014, 30 (28), 8598-8606 (28 pages).
Kuila, Tapas, et al. "Chemical functionalization of graphene and its applications," Progress in Materials Science 57 (2012) 1061-1105 (45 pages).
Lauffer, Peter, et al. "Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph, et al. "Adhesive Forces Between Aromatic Molecules and Graphene," The Journal of Physical Chemistry C 2014, 118(36), 20970-20981 (12 pages).
Lecourt, Thomas, et al."Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).
Li, Errui, et al. "Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).
Li, Junjie, et al. "Development of a colorimetric sensor array for the discrimination of aldehydes," Sensors and Actuators B 196 (2014) 10-17 (8 pages).
Li, Mingxiao, et al. "Preconcentration and Analysis of Trace Volatile Carbonyl Compounds," Anal Chem 2012, 84(3), 1288-1293 (6 pages).
Liu, Sophie F., et al. "Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).
Liu, Yuxin, et al. "Biological and Chemical Sensors based on Graphene Materials," Chem. Soc. Rev. 2012, 41 (6), 2283-2307 (27 pages).
Loh, Kian Ping, et al. "The Chemistry of Graphene," J. Mater. Chem., 2010, 20, 2277-2289 (13 pages).
Long, Brenda, et al. "Non-Covalent Functionalization of Graphene Using Self- Assembly of Alkane-Amines," Adv. Funct. Mater. 2012, 22, 717-725 (9 pages).
Lu, Chun-Hua, et al. "A Graphene Platform for Sensing Biomolecules," Angew. Chem. Int. Ed. 2009, 48, 4785-4787 (3 pages).
Machado, Roberto F., et al. "Detection of Lung Cancer by Sensor Array Analyses of Exhaled Breath," Am J Respir Crit Care Med, vol. 171, 1286-1291 (2005), 6 pages.
Mann, Jason A., et al. "Improving the Binding Characteristics of Tripodal Compounds on Single Layer Graphene," American Chemical Society 2013, vol. 7, No. 8, 7193-7199 (7 pages).

Manochehry, Sepehr, et al. "Optical biosensors utilizing graphene and functional DNA molecules," J. Mater. Res. 2017, 32(15), 2973-2983 (11 pages).
Mao, Shun, et al. "Specific Protein Detection Using Thermally Reduced Graphene Oxide Sheet Decorated with Gold Nanoparticle-Antibody Conjugates," Adv. Mater. 2010, 22, 3521-3526 (6 pages).
Meng, Zheng, et al. "Electrically-Transduced Chemical Sensors Based on Two- Dimensional Nanomaterials," Chem. Rev. 2019, 119, 478-598 (122 pages).
Nag, Sanada, et al. "Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).
Ohno, Yasuhide, et al. "Electrolyte-Gated Graphene Field-Effect Transistors for Detecting pH and Protein Adsorption," Nano Letters 2009, vol. 9, No. 9, 3318- 3322 (5 pages).
Olson, Eric J., et al. "Capacitive Sensing of Intercalated H2O Molecules Using Graphene," ACS Appl. Mater. Interfaces 2015, 7(46), 25804-25812 (29 pages).
Olson, Eric J., et al. "Getting More out of a Job Plot: Determination of Reactant to Product Stoichiometry in Cases of Displacement Reactions and nin Complex Formation," J. Org. Chem. 2011, 76, 8406-8412 (7 pages).
Pathipati, Srinivasa Rao, et al. "Modulation of charge transport properties of reduced graphene oxide by submonolayer physisorption of an organic dye," Organic Electronics 14 (2013) 1787-1792 (6 pages).
Peng, Gang, et al. "Diagnosing lung cancer in exhaled breath using gold nanoparticles," Nature nanotechnology, 2009, 4(10), 669-673 (5 pages).
Peressi, Maria "Surface Functionalization of Graphene," Graphene Chemistry, John Wiley & Sons, Ltd:2013, pp. 233-253 (21 pages).
Poli, Diana, et al. "Determination of aldehydes in exhaled breath of patients with lung cancer by means of on-fiber-derivatisation SPME-GC/MS," Journal of Chromatography B, 878 (2010) 2643- 2651 (9 pages).
Poulston, S., et al. "Surface Oxidation and Reduction of CuO and Cu2O Studied Using XPS and XAES," Surface and Interface Analysis, vol. 24, 811-820 (10 pages).
Putta, Chandrababu, et al. "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
Rekharsky, Mikhail V., et al. "Complexation Thermodynamics of Cyclodextrins," Chem. Rev. 1998, 98, 1875-1917 (44 pages).
Reuillard, B., et al. "Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).
Rodner, Marius, et al. "Graphene Decorated with Iron Oxide Nanoparticles for Highly Sensitive Interaction with Volatile Organic Compounds," Sensors 2019, 19, 918-026 (9 pages).
Rojas, Maria T., et al. "Supported Monolayers Containing Preformed Binding-Sites - Synthesis and Interfacial Binding-Properties of a Thiolated Beta-Cyclodextrin Derivative," J. Am. Chem. Soc. 1995, 117, 336-343 (8 pages).
Rushi, A.D., et al. "Exercising Substituents in porphyrins for real time selective sensing of volatile organic compounds," Sensors and Actuators B: Chemical, vol. 257, 2018, pp. 389-397 (9 pages).
Schedin, F., et al. "Detection of Individual Gas Molecules Adsorbed on Graphene," Nat. Mater. 2007, 6(9), 652-655 (11 pages).
Shao, Yuyan "Graphene Based Electrochemical Sensor and Biosensors: A Review," Electroanalysis 2010, 22, No. 10, 1027-1036 (10 pages).
Shao, Yuyan, et al. "Nitrogen-doped graphene and its electrochemical applications," J. Mater. Chem., 2010, 20, 7491-7496 (6 pages).
Song, Nan, et al. "Applications of pillarenes, an emerging class of synthetic macrocycles," Science China Chemistry, 2014, 57(9), 1185-1198 (15 pages).
Swanson, Emily, et al. "Self Assembly of Monolayers on Graphene with Pyrene and Cyclodextrin Derivatives," Research Poster. Elon University, LANDO program, Research Experience for Undergradu-

(56) References Cited

OTHER PUBLICATIONS ates Program of the National Science Foundation, Council of Undergraduate Research Experiences for Undergraduates symposium in Washington, D.C., Oct. 23-24, 2016 (1 page).
Terse-Thakoor, Trupti, et al. "Graphene based biosensors for healthcare," J. Mater. Res. 2017, 32(15), 2905-2929 (25 pages).
Turkevich, John, et al. "A study of the nucleation and growth processes in the synthesis of colloidal gold," Discuss. Faraday Soc., 1951, 11, 55-75 (23 pages).
Vincent, Mark A., et al. "Accurate Prediction of Adsorption Energies on Graphene, Using a Dispersion-Corrected Semiempirical Method Including Solvation," J. Chem. Inf. Model. 2014, 54, 2225-2260 (6 pages).
Vogel, Martin, et al. "Hydrazine reagents as derivatizing agents in environmental analysis -- a critical review," Fresenius J Anal Chem (2000) 366: 781-791 (11 pages).
Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).
Wang, Qing Hua, et al. "Room-temperature molecular-resolution characterization of self-assembled organic monolayers on epitaxial graphene," Nature Chemistry 2009 Vol. 1 (3), 206-211 (6 pages).
Wayu, Mulugeta B., et al. "Electropolymerization of Beta-Cyclodextrin onto Multi- Walled Carbon Nanotube Composite Films for Enhanced Selective Detection of Uric Acid," Journal of Electroanalytical Chemistry 783 (2016), 192-200 (9 pages).
Xi, Yuxi, et al. "Flexible Graphene Films via te Filtration of Water-Soluble Noncovalent Functionalized Graphene Sheets," J. Am. Chem. Soc. 2008, 130, 5856-5857 (2 pages).
Xu, Huifeng, et al. "Direct Electrochemixtry and electrocatalysis of hemoglobin protein entrapped in graphene and chitosan composite film," Talanta 81 (2010) 334-338 (5 pages).
Yavari, Fazel, et al. "Graphene-Based Chemical Sensors," J. Phys. Chem. Lett. 2012, 3, 1746-1753 (8 pages).
Zhang, Yao, et al. "Capacitive Sensing of Glucose in Electrolytes using Graphene Quantum Capacitance Varactors," ACS Appl. Mater. Interfaces 2017, 9, 38863- 38869 (7 pages).
Zhang, Yao, et al. "Glucose Sensing with Graphene Varactors," IEEE Sensors, SENSORS 2016 - Proceedings, Orlando, FL 2016 (3 pages).
Zhang, Yiheng, et al. "Direct Measurements of the Interaction between Pyrene and Graphite in Aqueous Media by Single Molecule Force Spectroscopy: Understanding the TT-TT Interactions," Langmuir 2007, 23, 7911-7915 (5 pages).
Zhao, Yan-Li, et al. "Noncovalent Functionalization of Single-Walled Carbon Nanotubes," Accounts of Chemical Research 2009, vol. 42, No. 8. 1161-1171 (12 pages).
Zhen, Xue, et al. "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
Zhu, Congzhi, et al. "Mingling Electronic Chemical Sensors with Supramolecular Host-Guest Chemistry," Current Organic Chemistry, 2014, 18, 1957-1964 (8 pages).
Zhu, Yanwu, et al. "Graphene and Graphene Oxide: Synthesis, Properties, and Applications," Adv. Mater. 2010, 22, 3906-3924 (19 pages).
"Non-Final Office Action," for U.S. Appl. No. 17/328,478 (our file 442.0383USU1) mailed Jun. 28, 2024 (36 pages).
"Response to Non-Final Rejection," mailed on May 8, 2024, for U.S. Appl. No. 17/387,503 (Pdsd 442.0320USC1), submitted via EFS-Web on Jul. 30, 2024, 9 pages.
"First Office Action," for Chinese Patent Application No. 202080058470.4 (our file 442.0372CNWO) mailed Sep. 12, 2023 (14 pages) with English Summary.
"International Preliminary Report on Patentability," for PCT Application No. PCT/US2022/019728 (our file 442.0388WOU1) mailed Sep. 28, 2023 (7 pages).
"Notice of Allowance," for U.S. Appl. No. 16/996,537 (our file 442.0372USU1) mailed Oct. 30, 2023 (13 pages).
"Office Action," for Japanese Patent Application No. 2022-570412 (our file 442.0383JPWO) mailed Oct. 31, 2023 (6 pages) with English Summary.
"Response to Communication Pursuant to Article 94(3) EPC," for European Patent Application No. 20764525.0 (our file 442.0372EPWO) filed Dec. 5, 2023 (121 pages).
"Response to Non-Final Rejection," mailed on Aug. 16, 2023, for U.S. Appl. No. 17/387,503 (Pdsd 442.0320USC1), submitted via EFS-Web on Nov. 7, 2023, 11 pages.
"Response to Non-Final Rejection," mailed on Jun. 27, 2023, for U.S. Appl. No. 16/996,537 (Pdsd 442.0372USU1), submitted via EFS-Web on Sep. 27, 2023, 20 pages.
"Communication Pursuant to Article 94(3) EPC," for European Patent Application No. 19709268.7 (our file 115.0320EPWO) mailed Sep. 13, 2022 (5 pages).
"International Search Report and Written Opinion," for PCT Application No. PCT/US2022/019728 (our file 115.0388WOU1) mailed Jun. 9, 2022 (11 pages).
"Non-Final Office Action," for U.S. Appl. No. 17/387,503 (our file 442.0320USC1) mailed May 8, 2024 (16 pages).
"Office Action," for Japanese Patent Application No. 2022-511117 (our file 442.0372JPWO) mailed Apr. 15, 2024 (10 pages) with English translation.
"Response to Final Rejection," mailed on Dec. 21, 2023, and Advisory Action mailed on Mar. 22, 2024, for U.S. Appl. No. 17/387,503 (Pdsd 442.0320USC1), submitted via EFS-Web on Apr. 19, 2024, 12 pages.
"Second Office Action," for Chinese Patent Application No. 202080058740.4 (our file 442.0372CNWO) mailed Apr. 27, 2024 (15 pages) with English translation.
Jin-Fa, Chen, et al. "Pillararene-based fluorescent chemosensors: recent advances and perspectives," Chemical Communications, 2017, vol. 53 No. 100, p. 13296-13311, 13296-13311.
Kirill, Puchnin, et al. "Field-effect transition sensor for KI detection based on self- assembled calixtube monolayers," Biosensors & Bioelectronics, 2017, vol. 98, pp. 140-146, 140-146.
Nuri, Kursunlu Ahmed, et al. "Preparation of pillar[5]arene-quinoline Langmuir- Blodgett thin films for detection of volatile organic compounds with host-guest principles," Analyst, 2017, vol. 142 No.19, pp. 3689-3698, 2017, 3689-3698.
"First Office Action," for Chinese Patent Application No. 201980014236.1 (our file 442.0320CNWO) mailed Jan. 20, 2023 (13 pages) with English summary.
"First Office Action," for Chinese Patent Application No. 201980027577.2 (our file 442.0325CNWO) mailed Feb. 10, 2023 (12 pages) with English summary.
"International Preliminary Report on Patentability," for PCT Application No. PCT/US2021/033872 (our file 115.0383WOU1) mailed Dec. 8, 2022 (7 pages).
"Response to Communication Pursuant to Rules 161(1) and 162 EPC," for European Patent Application No. 20764525.0 (our file 115.0372EPWO) filed Oct. 5, 2022 (27 pages).
"Non-Final Office Action," for U.S. Appl. No. 16/996,537 (our file 442.0372USU1) mailed Jun. 27, 2023 (57 pages).
"Non-Final Office Action," for U.S. Appl. No. 17/707,214 (our file 442.0325USC1) mailed Mar. 17, 2023 (42 pages).
"Office Action," for Japanese Patent Application No. 2022-511117 (our file 442.0372JPWO) mailed May 23, 2023 (12 pages), with English translation.
"Response to Communication Pursuant to Article 94(3) EPC," for European Patent Application No. 19709268.7 (our file 442.0320EPWO) filed Mar. 22, 2023 (12 pages).
"Response to Non-Final Rejection," mailed on Mar. 17, 2023 for U.S. Appl. No. 17/707,214 (Pdsd 442.0325USC1), submitted via EFS-Web on Jun. 13, 2023, 8 pages.
"Second Office Action," for Chinese Patent Application No. 201980014236.1 (our file 442.0320CNWO) mailed Mar. 29, 2023 (6 pages) with English summary.

(56) References Cited

OTHER PUBLICATIONS

Li, C., et al. "The Electrochemical Sensor Based on Electrochemical Oxidation of Nitrite on Metalloporphyrin-Graphene Modified Glassy Carbon Electrode," Royal Society of Chemistry, 2016, 6, 90480 (9 pages).

Wang, Aijian, et al. "Graphene and Carbon-Nanotube Nanohybrids Covalently Functionalized by Porphyrins and Phthalocyanines for Optoelectronic Properties," Advanced Materials, 2018, 30, 1705704 (9 pages).

"Final Office Action," for U.S. Appl. No. 17/387,503 (our file 442.0320USC1) mailed Dec. 21, 2023 (19 pages).

"Response to Final Rejection," mailed on Dec. 21, 2023, for U.S. Appl. No. 17/387,503 (Pdsd 442.0320USC1), submitted via EFS-Web on Mar. 12, 2024, 12 pages.

"Communication Pursuant to Article 94(3) EPC," for European Patent Application No. 20764525.0 (our file 442.0372EPWO) mailed Aug. 16, 2023 (6 pages).

"Non-Final Office Action," for U.S. Appl. No. 17/387,503 (our file 442.0320USC1) mailed Aug. 16, 2023 (51 pages).

"Notice of Allowance," for U.S. Appl. No. 17/707,214 (our file 442.0325USC1) mailed Aug. 29, 2023 (18 pages).

"Second Office Action," for Chinese Patent Application No. 201980027577.2 (our file 442.0325CNWO) mailed Aug. 18, 2023 (4 pages) with English Summary.

Seo, Sohyeon, et al."A Molecular Approach to an Electrostatic Hydrogen Evolution Reaction on Single-Layer Graphene," Nanoscale 9.11 (2017): 3969- 3979 (11 pages).

ALDEHYDE AND KETONE RECEPTOR MODIFICATION OF GRAPHENE

This application claims the benefit of U.S. Provisional Application No. 63/161,640, filed Mar. 16, 2021, the content of which is herein incorporated by reference in its entirety.

FIELD

Embodiments herein relate to chemical sensors, devices and systems including the same, and related methods. More specifically, embodiments herein relate to chemical sensors based on the non-covalent surface modification of graphene with compounds containing hydrazine or hydroxylamine functional groups for the detection of aldehyde and ketone-bearing analytes.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. In particular, the volatile organic compounds can include aldehydes and ketones, which are known biomarkers for disease and can be detected in a gaseous sample. The detection of these compounds or differential sensing of the same can allow for the early detection of particular disease states.

SUMMARY

In a first aspect, a medical device having a graphene varactor is included. The graphene varactor includes a graphene layer, having a self-assembled monolayer disposed on an outer surface of the graphene layer through electrostatic interactions between a partial positive charge on hydrogen atoms of one or more hydrocarbons of the self-assembled monolayer and π-electron system of graphene. The self-assembled monolayer includes one or more compounds can include one or more hydrazine groups or hydroxylamine groups, substituted hydrazine or hydroxylamine groups, or derivatives thereof.

In a second aspect, in addition to one or more of the preceding or following aspects, or in the alternative to some aspects, the self-assembled monolayer provides a Langmuir theta value of at least 0.9.

In a third aspect, in addition to one or more of the preceding or following aspects, or in the alternative to some aspects, the self-assembled monolayer provides coverage over the graphene from 50% to 150% by surface area.

In a fourth aspect, in addition to one or more of the preceding or following aspects, or in the alternative to some aspects, the self-assembled monolayer further includes an acidic compound effective to catalyze a reaction between the hydrazine groups or hydroxylamine groups and an aldehyde or ketone.

In a fifth aspect, in addition to one or more of the preceding or following aspects, or in the alternative to some aspects, the self-assembled monolayer can include compounds of a formula:

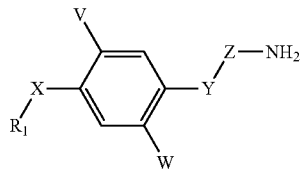

wherein Z includes NH or O, wherein $R^1$ includes $(CH_2)_mCH_3$, wherein 50>m>5, wherein X includes $CH_2$, O, NH, $N(CH_2)_nCH_3$, —C(=O)O—, —OC(=O)—, —C(=O)NH—, —NHC(=O)—, —C(=O)N((CH_2)_nCH_3)—, —N((CH_2)_nCH_3)C(=O)—, —S—, —S(=O)—, —S(=O)_2—, —S(=O)_2O—, —OS(=O)_2—, —S(=O)_2NH—, —NHS(=O)_2—, —S(=O)_2N((CH_2)_nCH_3)—, —N((CH_2)_nCH_3)S(=O)_2—, and wherein n is 0, or 1 to 20, wherein Y includes $(C_6H_4)_p$ or $(CH_2)_p$, wherein p is 0, 1, or 2, wherein W includes H, $(CH_2)_qOH$, $(CH_2)_qCOOH$, $(CH_2)_qSO_2OH$, or $(CH_2)_qPO_2OH$, wherein q is 0, 1, or 2, wherein V includes H, NO, $NO_2$, Cl, Br, I, F, $CF_3$, —CN, —NC, $C_6H_5$ (phenyl), OR, —C(=O)R, SR, COOR, OCOOR, —S(=O)R, —S(=O)_2R, —S(=O)_2OR, —OS(=O)_2R, —S(=O)_2NHR, —NHS(=O)_2R, —S(=O)_2NRR^2, —NR^2S(=O)_2R, wherein R and $R^2$ include $(CH_2)_kCH_3$ and k is 0, 1, or 2, wherein $R^1X$ and V can be present in any ring position relative to a $YZNH_2$ group and W is present in an alpha position relative to the $YZNH_2$ to provide proximity between W and $YZNH_2$, and any tautomers thereof.

In a sixth aspect, in addition to one or more of the preceding or following aspects, or in the alternative to some aspects, wherein W is present in the alpha position effective to permit interaction of an acidic hydrogen atom on W with an aldehyde molecule so as to catalyze a reaction of the aldehyde with the hydrazine group or hydroxylamine group.

In a seventh aspect, in addition to one or more of the preceding or following aspects, or in the alternative to some aspects, the formula includes more than one $R^1X$ moiety effective to induce self-assembly of the compound.

In an eighth aspect, in addition to one or more of the preceding or following aspects, or in the alternative to some aspects, the formula includes more than one V moiety effective to provide electron density to the compound.

In a ninth aspect, in addition to one or more of the preceding or following aspects, or in the alternative to some aspects, the self-assembled monolayer can include compounds of the formula:

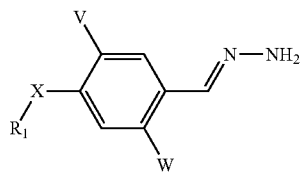

wherein $R^1$ includes $(CH_2)_mCH_3$, wherein 50>m>5, wherein X includes $CH_2$, O, NH, $N(CH_2)_nCH_3$, —C(=O)O—, —OC(=O)—, —C(=O)NH—, —NHC(=O)—, —C(=O)N((CH_2)_nCH_3)—, —N((CH_2)_nCH_3)C(=O)—, —S—, —S(=O)—, —S(=O)_2—, —S(=O)_2O—, —OS(=O)_2—, —S(=O)_2NH—, —NHS(=O)_2—, —S(=O)_2N((CH_2)_nCH_3)—, —N((CH_2)_nCH_3)S(=O)_2—, and wherein n is 0, or 1 to 20, wherein W includes H, $(CH_2)_qOH$, $(CH_2)_qCOOH$, $(CH_2)_qSO_2OH$, or $(CH_2)_qPO_2OH$, wherein q is 0, 1, or 2, wherein V includes H, NO, $NO_2$, Cl, Br, I, F, CF$_3$, —CN, —NC, C$_6$H$_5$ (phenyl), OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$_2$S(=O)$_2$R, wherein R and R$^2$ include (CH$_2$)$_k$CH$_3$ and k is 0, 1, or 2, wherein R$^1$X and V can be present in any ring position relative to an NNH$_2$ group and W is present in an alpha position relative to the NNH$_2$ group, and any tautomers thereof.

In a tenth aspect, in addition to one or more of the preceding or following aspects, or in the alternative to some aspects, wherein W is present in the alpha position effective to permit interaction of an acidic hydrogen atom on W with an aldehyde molecule so as to catalyze a reaction of the aldehyde with the hydrazine group or hydroxylamine group.

In an eleventh aspect, in addition to one or more of the preceding or following aspects, or in the alternative to some aspects, the self-assembled monolayer can include compounds of the formula:

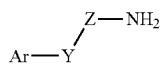

wherein Z includes NH or O, where Y includes (CH$_2$)$_p$, wherein p is from 0 to 20, wherein Ar includes an aromatic substituent with 16 or more aromatic carbons, and any tautomers thereof.

In a twelfth aspect, in addition to one or more of the preceding or following aspects, or in the alternative to some aspects, the aromatic substituent includes naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof.

In a thirteenth aspect, in addition to one or more of the preceding or following aspects, or in the alternative to some aspects, the aromatic substituent further includes one or more substitutions including (CH$_2$)$_q$OH, (CH$_2$)$_q$COOH, (CH$_2$)$_q$SO$_2$OH, or (CH$_2$)$_q$PO$_2$OH, in a position alpha to a YZNH$_2$ group effective to permit interaction of an acidic hydrogen atom on the substitution with an aldehyde molecule so as to catalyze a reaction of the aldehyde with the hydrazine or hydroxylamine group.

In a fourteenth aspect, in addition to one or more of the preceding or following aspects, or in the alternative to some aspects, the self-assembled monolayer can include compounds of the formula:

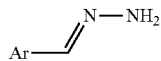

wherein Ar includes an aromatic substituent with 16 or more aromatic carbons, and any tautomers thereof.

In a fifteenth aspect, in addition to one or more of the preceding or following aspects, or in the alternative to some aspects, the aromatic substituent includes naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof.

In a sixteenth aspect, in addition to one or more of the preceding or following aspects, or in the alternative to some aspects, the aromatic substituent further includes one or more substitutions including (CH$_2$)$_q$OH, (CH$_2$)$_q$COOH, (CH$_2$)$_q$SO$_2$OH, or (CH$_2$)$_q$PO$_2$OH, in a position alpha to a NNH$_2$ group effective to permit interaction of an acidic hydrogen atom on the substitution with an aldehyde molecule.

In a seventeenth aspect, a method of modifying a surface of graphene to create a graphene varactor, the method is included, the method including forming a self-assembled monolayer disposed on an outer surface of the graphene layer through electrostatic interactions between a partial positive charge on hydrogen atoms of more hydrocarbons of the self-assembled monolayer and π-electron system of graphene, the self-assembled monolayer can include one or more compounds can include hydrazine or hydroxylamine groups, substituted hydrazine or hydroxylamine groups, or derivatives thereof.

In an eighteenth aspect, in addition to one or more of the preceding or following aspects, or in the alternative to some aspects, the method can further include quantifying an extent of surface coverage of the self-assembled monolayer using contact angle goniometry, Raman spectroscopy, or x-ray photoelectron spectroscopy.

In a nineteenth aspect, a method for detecting an analyte is included, the method including collecting a gaseous sample from a patient, contacting the gaseous sample with one or more graphene varactors, each of the one or more graphene varactors can include a graphene layer, a self-assembled monolayer disposed on an outer surface of the graphene layer through electrostatic interactions between a partial positive charge on hydrogen atoms of more hydrocarbons of the self-assembled monolayer and π-electron system of graphene, and wherein the self-assembled monolayer includes at least one selected from the group consisting of compounds can include hydrazine or hydroxylamine groups, substituted hydrazine or hydroxylamine groups, or derivatives thereof.

In a twentieth aspect, in addition to one or more of the preceding or following aspects, or in the alternative to some aspects, the method can further include measuring a differential response in an electrical property of the one or more graphene varactors due to binding of one or more analytes present in the gaseous sample. This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
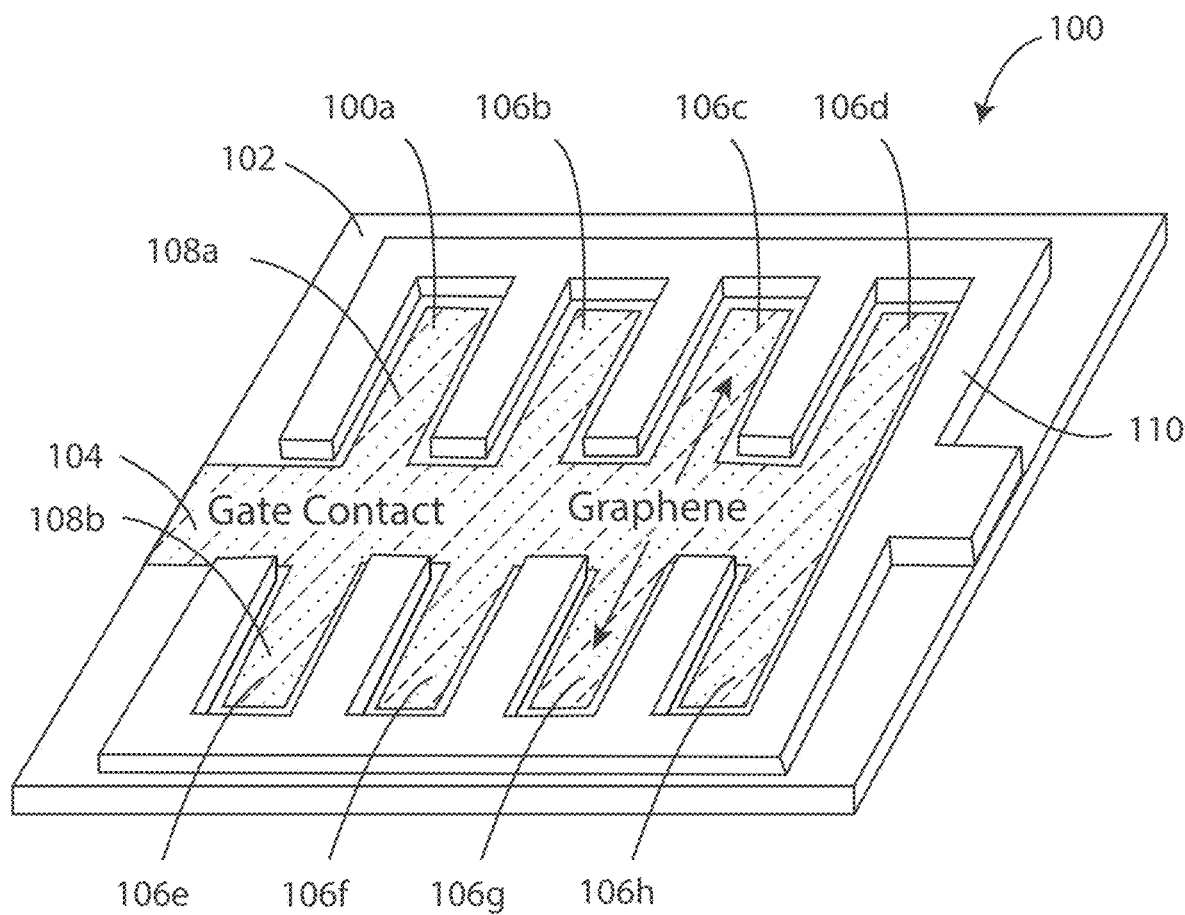
FIG. 1 is a schematic perspective view of a graphene varactor in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Aldehydes and ketones are two main classes of organic compounds and are prevalent in a variety of samples, notably gaseous samples. Some aldehydes, such as formaldehyde, can negatively affect people's health, and several aldehydes and ketones are known biomarkers of disease that can be detected as analytes in human breath. In one example, elevated levels of C1-C10 aldehydes in human breath can be a marker of lung cancer, and in particular one aldehyde, hexanal ($C_6E_{12}O$), is known to be one of the predominant biomarkers of oxidative stress in tumors. In another example, breath ketones, such as acetone, can be indicative of a metabolic state of a patient or of certain disease states such as diabetic ketoacidosis.

In accordance with various embodiments herein, determining the presence of analytes in gaseous samples is accomplished by the derivatization of certain classes of chemical compounds with specific reactivity with aldehydes and ketones. For example, carbonyl specific derivatization agents herein, which target aldehydes and ketones, can include nitrogen containing groups such as amines, hydroxylamines, or hydrazines, which react with carbonyl groups on aldehydes and ketones in a condensation reaction to form imines, oximes, and hydrazones, respectively. By way of example, embodiments herein can include chemical sensors having surface functionalization with self-assembled monolayers including one or more of a) amines, b) O-hydroxylamines, and c) hydrazines that detect aldehydes by way of the following general condensation reactions:

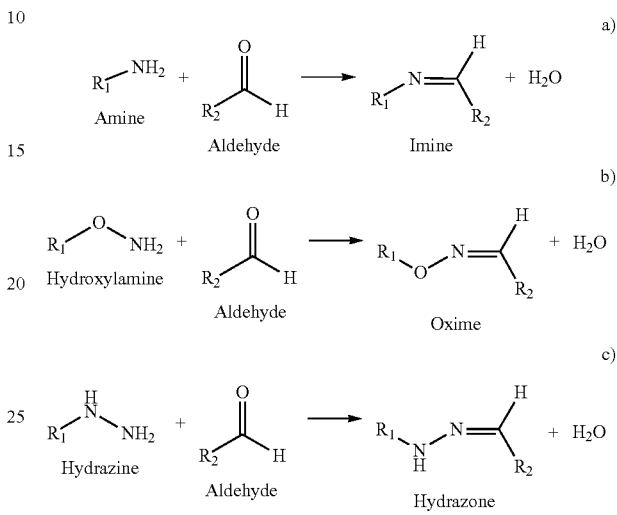

Embodiments herein relate to chemical sensors, medical devices and systems including the same, and related methods for detecting chemical compounds in gaseous samples, such as, but not limited to, in the breath of a patient. In some embodiments, the chemical sensors herein can be based on the non-covalent surface modification of graphene. In various embodiments, compounds containing hydrazine and hydroxylamine functional groups are used in the self-assembly of such compounds onto graphene surfaces. The self-assembly is achieved through the inclusion of long alkyl chains (e.g., C1-C50) on the hydrazine and hydroxylamine containing compounds that provide CH-π interactions between graphene and the compounds, in addition to electrostatic interactions and π-π stacking interactions.

Graphene is a form of carbon containing a single layer of carbon atoms in a hexagonal lattice. Graphene has a high strength and stability due to its tightly packed sp$^2$ hybridized orbitals, where each carbon atom forms one sigma (σ) bond each with its three neighboring carbon atoms and has one p orbital projected out of the hexagonal plane. The p orbitals of the hexagonal lattice can hybridize to form a π bond on the surface of graphene that is suitable for non-covalent electrostatic interaction and π-π stacking interactions with other molecules.

Without wishing to be bound by any particular theory, it is believed that hydrogen atoms within hydrocarbon groups (e.g., alkyl chains) can interact with the π electron system on the surface of graphene through electrostatic interactions. Hydrogen atoms have low electronegativity, and as such, they carry a partial positive charge. The partial positive charge on the hydrogen atoms of alkyl chains can participate in electrostatic interactions with the π electron system of the π band on the surface of graphene. The alkyl chains can adsorb onto the graphene surface in an all trans conformation along the carbon-carbon backbone, such that all carbon atoms fall into one plane that is either perpendicular or parallel to the graphene surface.

By way of example, the trans conformation of an alkyl chain having a perpendicular orientation of its carbon-carbon backbone along the surface of graphene creates a configuration where every second —CH$_2$— group of the alkyl chain has its hydrogen atoms pointing towards the graphene. As such, alkyl chains can orient themselves with respect to the graphene surface so that the —CH$_2$— hydrogens of alternate —CH$_2$— groups are disposed the same distance from the graphene surface and the hydrogen-graphene interactions are maximized. By way of another example, the trans conformation of an alkyl chain having a parallel orientation of its carbon-carbon backbone along the surface of graphene creates a configuration where every —CH$_2$— group of the alkyl chain has one hydrogen atom pointing towards the graphene. As such, alkyl chains can also orient themselves with respect to the graphene surface so that the —CH$_2$— hydrogens of alternate —CH$_2$— groups are disposed the same distance from the graphene surface and the hydrogen-graphene interactions are maximized. In either conformation, the alkyl chain can interact with the surface of graphene along the length of the alkyl chain. It is also believed that the hydrogen atoms of alkenyl chains and alkynyl chains, and derivatives thereof, can similarly interact with the graphene surface.

The non-covalent functionalization of graphene with a self-assembled monolayer does not significantly affect the atomic structure of graphene, and provides a stable graphene-based sensor with high sensitivity towards a number of volatile organic compounds (VOCs) in the parts-per-billion (ppb) or parts-per-million (ppm) levels. As such, the embodiments herein can be used to detect VOCs and/or differential binding patterns of the same that, in turn, can be used to identify disease states.

Various graphene-based varactors containing a single layer of carbon atoms are contemplated herein. Referring now to FIG. 1, a schematic view of a graphene-based variable capacitor (or graphene varactor) 100 is shown in accordance with the embodiments herein. It will be appreciated that graphene varactors can be prepared in various ways with various geometries, and that the graphene varactor shown in FIG. 1 is just one example in accordance with the embodiments herein.

Graphene varactor 100 can include an insulator layer 102, a gate electrode 104 (or "gate contact"), a dielectric layer (not shown in FIG. 1), one or more graphene layers, such as graphene layers 108*a* and 108*b*, and a contact electrode 110 (or "graphene contact"). In some embodiments, the graphene layer(s) 108*a-b* can be contiguous, while in other embodiments the graphene layer(s) 108*a-b* can be non-contiguous. Gate electrode 104 can be deposited within one or more depressions formed in insulator layer 102. Insulator layer 102 can be formed from an insulative material such as silicon dioxide, formed on a silicon substrate (wafer), and the like. Gate electrode 104 can be formed by an electrically conductive material such as chromium, copper, gold, silver, tungsten, aluminum, titanium, palladium, platinum, iridium, and any combinations or alloys thereof, which can be deposited on top of or embedded within the insulator layer 102. The dielectric layer can be disposed on a surface of the insulator layer 102 and the gate electrode 104. The graphene layer(s) 108*a-b* can be disposed on the dielectric layer. The dielectric layer will be discussed in more detail below in reference to FIG. 2.

Graphene varactor 100 includes eight gate electrode fingers 106*a*-106*h*. It will be appreciated that while graphene varactor 100 shows eight gate electrode fingers 106*a*-106*h*, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 100 can include one or more contact electrodes 110 disposed on portions of the graphene layers 108*a* and 108*b*. Contact electrode 110 can be formed from an electrically conductive material such as chromium, copper, gold, silver, tungsten, aluminum, titanium, palladium, platinum, iridium, and any combinations or alloys thereof. Further aspects of exemplary graphene varactor construction can be found in U.S. Pat. No. 9,513,244, the content of which is herein incorporated by reference in its entirety.

The graphene varactors described herein can include those in which a single graphene layer has been surface-modified through non-covalent electrostatic interactions between graphene and molecules substituted with hydrocarbon groups, such as, for example, the compounds containing hydrazine and hydroxylamine functional groups as described herein. In some embodiments, the surface of a single graphene layer can be surface modified through non-covalent interactions between graphene and any one of a number of compounds containing aromatic substituent containing 16 or more aromatic carbon atoms and containing hydrazine and hydroxylamine functional groups. The aromatic substituent can include naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof. Additional substitutions for the compounds suitable for use herein are described below. Details regarding the graphene varactors and π-electron-rich molecules suitable for use herein will also be discussed more fully below.

Figure 2:
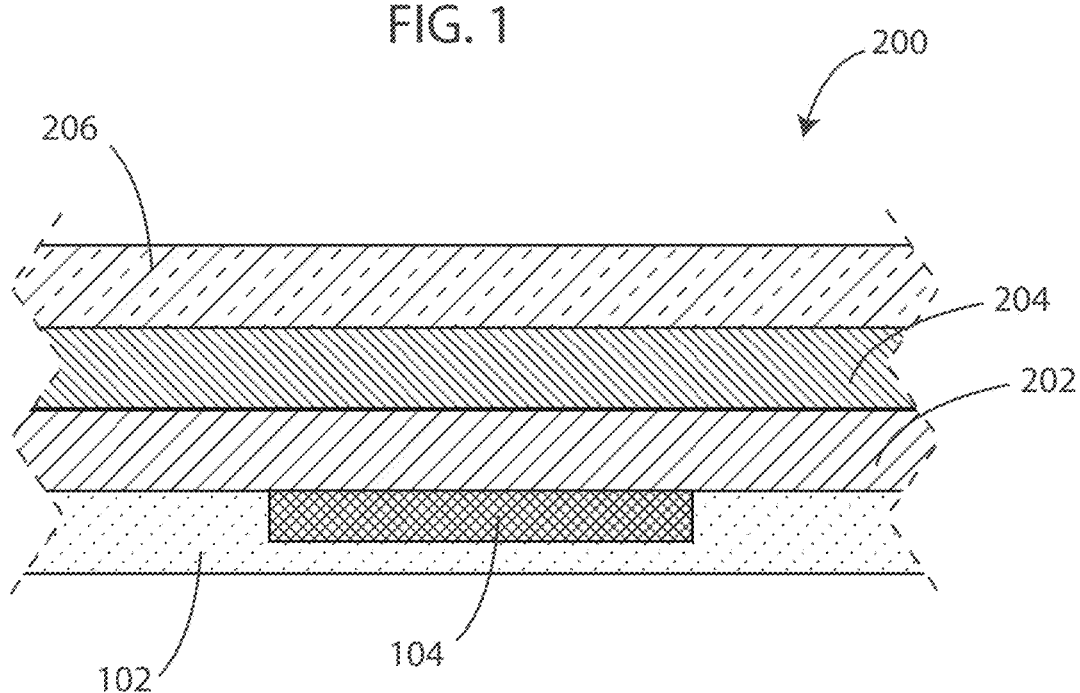
FIG. 2 is a schematic cross-sectional view of a portion of a graphene varactor in accordance with various embodiments herein.

Referring now to FIG. 2, a schematic cross-sectional view of a portion of a graphene varactor 200 is shown in accordance with various embodiments herein. The graphene varactor 200 can include an insulator layer 102 and a gate electrode 104 recessed into the insulator layer 102. The gate electrode 104 can be formed by depositing an electrically conductive material in the depression in the insulator layer 102, as discussed above in reference to FIG. 1. A dielectric layer 202 can be formed on a surface of the insulator layer 102 and the gate electrode 104. In some examples, the dielectric layer 202 can be formed of a material, such as, silicon dioxide, aluminum oxide, hafnium dioxide, zirconium dioxide, hafnium silicate, or zirconium silicate.

The graphene varactor 200 can include a single graphene layer 204 that can be disposed on a surface of the dielectric layer 202. The graphene layer 204 can be surface modified with a self-assembled monolayer 206. The self-assembled monolayer 206 can be formed of a homogenous population of π-electron-rich molecules disposed on an outer surface of the graphene layer 204 through non-covalent electrostatic interactions. Exemplary π-electron-rich molecules are described more fully below. The self-assembled monolayer 206 can provide at least 90% surface coverage (by area) of the graphene layer 204. In some embodiments, the self-assembled monolayer 206 can provide at least 95% surface coverage of the graphene layer 204. In other embodiments, the self-assembled monolayer 206 can provide at least 98% surface coverage of the graphene layer 204.

In some embodiments, the self-assembled monolayer can provide at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 100% surface coverage (by area) of the graphene layer. It will be appreciated that the self-assembled monolayer can provide surface coverage falling within a range wherein any of the forgoing percentages can serve as the lower or upper bound of the range, provided that the lower bound of the range is a value less than the upper bound of the range.

In some embodiments, it will be appreciated that the self-assembly of π-electron-rich molecules on the surface of the graphene layer can include the self-assembly into more than a monolayer, such as a multilayer. Multilayers can be detected and quantified by techniques such as scanning tunneling microscopy (STM) and other scanning probe microscopies. References herein to a percentage of coverage greater than 100% shall refer to the circumstance where a portion of the surface area is covered by more than a monolayer, such as covered by two, three or potentially more layers of the compound used. Thus, a reference to 105% coverage herein shall indicate that approximately 5% of the surface area includes more than monolayer coverage over the graphene layer. In some embodiments, graphene surfaces can include 101%, 102%, 103%, 104%, 105%, 110%, 120%, 13%, 140%, 150%, or 175% surface coverage of the graphene layer. It will be appreciated that multilayer surface coverage of the graphene layer can fall within a range of surface coverages, wherein any of the forgoing percentages can serve as the lower or upper bound of the range, provided that the lower bound of the range is a value less than the upper bound of the range. For example, ranges of coverage can include, but are not limited to, 50% to 150% by surface area, 80% to 120% by surface area, 90% to 110%, or 99% to 120% by surface area.

In some embodiments, the self-assembled monolayers suitable for use herein can provide coverage of the graphene surface with a monolayer as quantified by the Langmuir theta value of at least some minimum threshold value, but avoid covering the majority of the surface of the graphene with a multilayer thicker than a monolayer. Details about the Langmuir theta values and determination of thereof for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98. In some embodiments, the self-assembled monolayers can provide a Langmuir theta value of at least 0.85, 0.86, 0.87, 0.88, 0.89, 0.90, 0.91, 0.92, 0.93, 0.94, 0.95, 0.96, 0.97, 0.98, 0.99, or 1.0. It will be appreciated that the self-assembled monolayer can provide a range of Langmuir theta values, wherein any of the forgoing Langmuir theta values can serve as the lower or upper bound of the range, provided that the lower bound of the range is a value less than the upper bound of the range.

Figure 3:
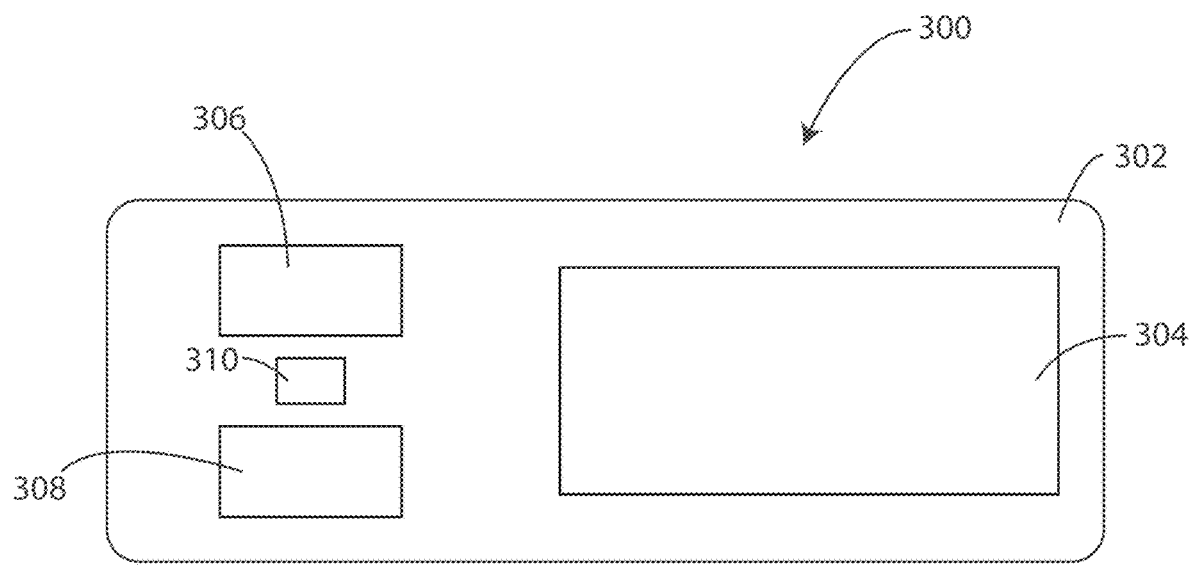
FIG. 3 is a schematic top plan view of a chemical sensor element in accordance with various embodiments herein.

Referring now to FIG. 3, a schematic top plan view of a chemical sensor element 300 is shown in accordance with various embodiments herein. The chemical sensor element 300 can include a substrate 302. It will be appreciated that the substrate can be formed from many different materials. By way of example, the substrate can be formed from silicon, glass, quartz, sapphire, polymers, metals, glasses, ceramics, cellulosic materials, composites, metal oxides, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the length (or major axis) can be from about 20 µm to about 1 cm. In some embodiments, the width (perpendicular to the major axis) can be from about 0.2 cm to about 8 cm. In some embodiments, the width (perpendicular to the major axis) can be from about 20 µm to about 0.8 cm. In some embodiments, the graphene-based chemical sensor can be disposable.

A first measurement zone 304 can be disposed on the substrate 302. In some embodiments, the first measurement zone 304 can define at least a portion of a first gas flow path. The first measurement zone (or gas sample zone) 304 can include a plurality of discrete graphene-based variable capacitors (or graphene varactors) that can sense analytes in a gaseous sample, such as a breath sample. A second measurement zone (or environment sample zone) 306, separate from the first measurement zone 304, can also be disposed on the substrate 302. The second measurement zone 306 can define at least a portion of a second gas flow path. In some embodiments, the second gas flow path can be separate from the first gas flow path.

The second measurement zone 306 can also include a plurality of discrete graphene varactors. In some embodiments, the second measurement zone 306 can include the same (in type and/or number) discrete graphene varactors that are within the first measurement zone 304. In some embodiments, the second measurement zone 306 can include only a subset of the discrete graphene varactors that are within the first measurement zone 304. In operation, the data gathered from the first measurement zone 304, which can be reflective of the gaseous sample analyzed, can be corrected or normalized based on the data gathered from the second measurement zone, which can be reflective of analytes present in the environment.

In some embodiments, a third measurement zone (drift control or witness zone) 308 can also be disposed on the substrate. The third measurement zone 308 can include a plurality of discrete graphene varactors. In some embodiments, the third measurement zone 308 can include the same (in type and/or number) discrete graphene varactors that are within the first measurement zone 304. In some embodiments, the third measurement zone 308 can include only a subset of the discrete graphene varactors that are within the first measurement zone 304. In some embodiments, the third measurement zone 308 can include discrete graphene varactors that are different than those of the first measurement zone 304 and the second measurement zone 306. Aspects of the third measurement zone are described in greater detail below. The third measurement zone 308 can define at least a portion of a third gas flow path. In some embodiments, the third gas flow path can be separate from the first gas flow path and the second gas flow path.

The first measurement zone 304, the second measurement zone 306, and the third measurement zone 308 can be the same size or can be of different sizes. The chemical sensor element 300 can also include a component 310 to store reference data. The component 310 to store reference data can be an electronic data storage device, an optical data storage device, a printed data storage device (such as a printed code), or the like. The reference data can include, but is not limited to, data regarding the third measurement zone 308 (described in greater detail below).

In some embodiments, chemical sensor elements embodied herein can include electrical contacts (not shown) that can be used to provide power to components on the chemical sensor element 300 and/or can be used to read data regarding the measurement zones and/or data from the stored in component 310. However, in other embodiments there are no external electrical contacts on the chemical sensor element 300.

Figure 4:
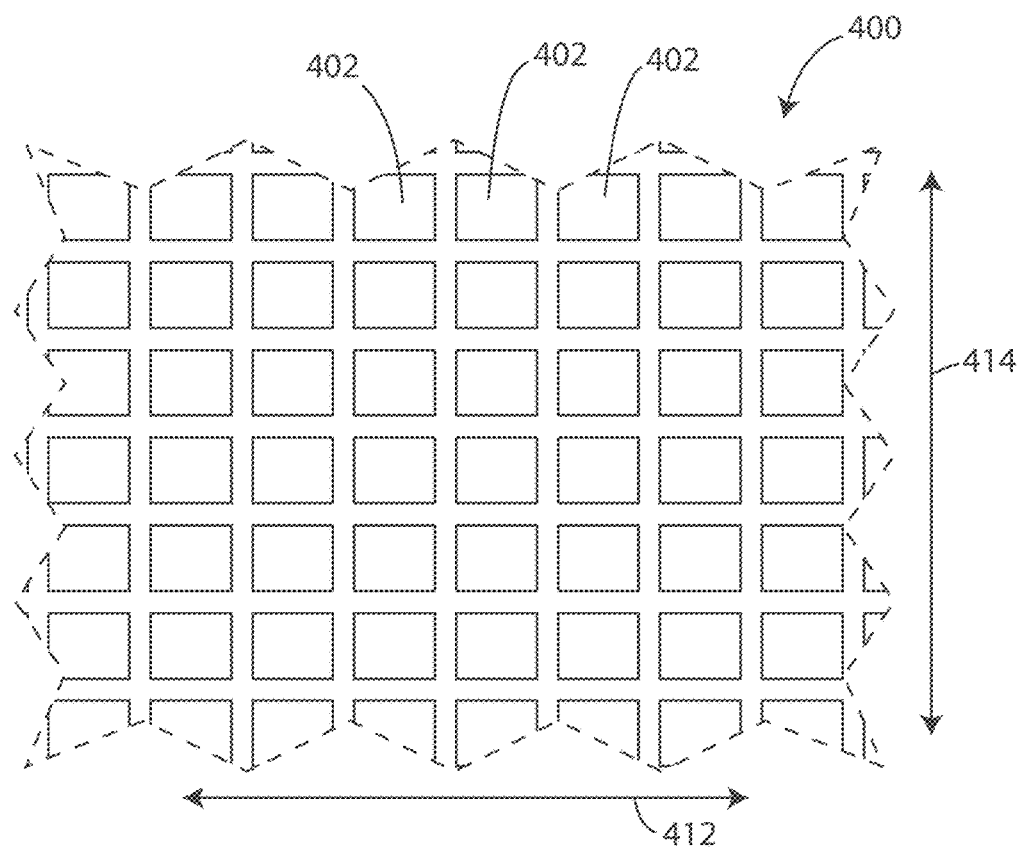
FIG. 4 is a schematic diagram of a portion of a measurement zone in accordance with various embodiments herein.

Referring now to FIG. 4, a schematic diagram of a portion of a measurement zone 400 is shown in accordance with various embodiments herein. A plurality of discrete graphene varactors 402 can be disposed within the measurement zone 400 in an array. In some embodiments, a chemical sensor element can include a plurality of graphene varactors configured in an array within a measurement zone. In some embodiments, the plurality of graphene varactors can be identical, while in other embodiments the plurality of graphene varactors can be different from one another.

In some embodiments, the discrete graphene varactors can be heterogeneous in that they are all different from one another in terms of their binding behavior or specificity with regard to a particular analyte. In some embodiments, some discrete graphene varactors can be duplicated for validation purposes, but are otherwise heterogeneous from other discrete graphene varactors. Yet in other embodiments, the discrete graphene varactors can be homogeneous. While the discrete graphene varactors 402 of FIG. 4 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 402 across the length 412 and width 414 of the measurement zone can be substantially random. In other embodiments, the order can be specific. For example, in some embodiments, a measurement zone can be ordered so that the specific discrete graphene varactors 402 for analytes having a lower molecular weight are located farther away from the incoming gas flow relative to specific discrete graphene varactors 402 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors within a particular measurement zone can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

Each of the discrete graphene varactors suitable for use herein can include at least a portion of one or more electrical circuits. By way of example, in some embodiments, each of the discrete graphene varactors can include one or more passive electrical circuits. In some embodiments, the graphene varactors can be included such that they are integrated directly on an electronic circuit. In some embodiments, the graphene varactors can be included such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a gas sample.

Figure 5:
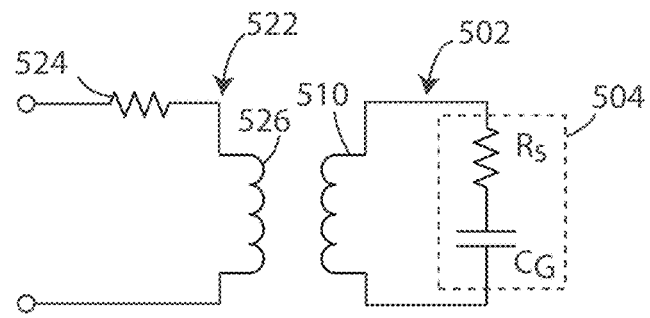
FIG. 5 is a circuit diagram of a passive sensor circuit and a portion of a reading circuit in accordance with various embodiments herein.

It will be appreciated that the chemical sensor elements embodied herein can include those that are compatible with passive wireless sensing. A schematic diagram of a passive sensor circuit 502 and a portion of a reading circuit 522 is shown in FIG. 5 and discussed in more detail below. In the passive wireless sensing arrangement, the graphene varactor(s) can be integrated with an inductor such that one terminal of the graphene varactor contacts one end of the inductor, and a second terminal of the graphene varactor contacts a second terminal of the inductor. In some embodiments, the inductor can be located on the same substrate as the graphene varactor, while in other embodiments, the inductor can be located in an off-chip location.

Referring now to FIG. 5, a schematic diagram of a passive sensor circuit 502 and a portion of a reading circuit 522 is shown in accordance with various aspects herein. In some embodiments, the passive sensor circuit 502 can include a metal-oxide-graphene varactor 504 (wherein RS represents the series resistance and CG represents the varactor capacitor) coupled to an inductor 510. Graphene varactors can be prepared in various ways and with various geometries. By way of example, in some aspects, a gate electrode can be recessed into an insulator layer as shown as gate electrode 104 in FIG. 1. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a metal oxide such as, aluminum oxide, hafnium dioxide, zirconium dioxide, silicon dioxide, or of another material such as hafnium silicate or zirconium silicate. A surface-modified graphene layer can be disposed on the dielectric layer. Contact electrodes can also be disposed on a surface of the surface-modified graphene layer, also shown in FIG. 1 as contact electrode 110.

In various embodiments, the functionalized graphene layer (e.g., functionalized to include analyte binding receptors), which is part of the graphene varactor and thus part of a sensor circuit, such as a passive sensor circuit, is exposed to the gas sample flowing over the surface of the measurement zone. The passive sensor circuit 502 can also include an inductor 510. In some embodiments, only a single varactor is included with each passive sensor circuit 502. In other embodiments, multiple varactors are included, such as in parallel, with each passive sensor circuit 502.

In the passive sensor circuit 502, the capacitance of the electrical circuit changes upon binding of an analyte in the gas sample and the graphene varactor. The passive sensor circuit 502 can function as an LRC resonator circuit, wherein the resonant frequency of the LRC resonator circuit changes upon binding with a component from a gas sample.

The reading circuit 522 can be used to detect the electrical properties of the passive sensor circuit 502. By way of example, the reading circuit 522 can be used to detect the resonant frequency of the LRC resonator circuit and/or changes in the same. In some embodiments, the reading circuit 522 can include a reading coil having a resistance 524 and an inductance 526. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and/or the value of the phase dip frequency.

Figure 6:
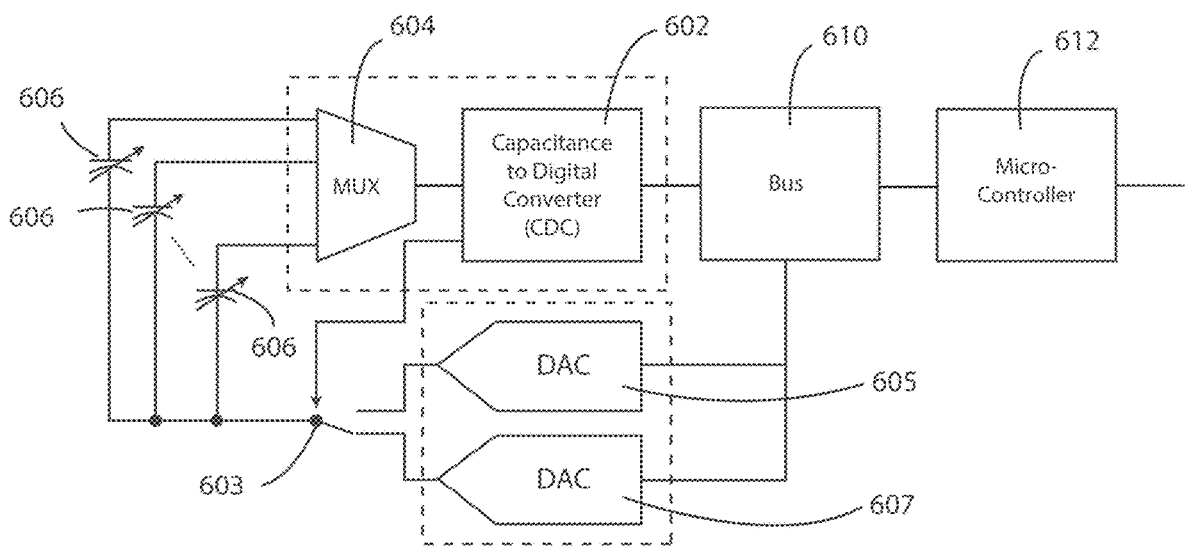
FIG. 6 is a schematic diagram of circuitry to measure the capacitance of a plurality of discrete graphene varactors in accordance with various embodiments herein.

Other types of readout circuitry for the graphene varactors are also contemplated herein. For example, referring now to FIG. 6, a schematic diagram is shown of another embodiment of circuitry to measure the capacitance of a plurality of discrete graphene varactors in accordance with various embodiments herein. The circuitry can include a capacitance to digital converter (CDC) 602 in electrical communication with a multiplexor 604. The multiplexor 604 can provide selective electrical communication with a plurality of graphene varactors 606. The connection to the other side of the graphene varactors 606 can be controlled by a switch 603 (as controlled by the CDC) and can provide selective electrical communication with a first digital to analog converter (DAC) 605 and a second digital to analog converter (DAC) 607. The other side of the DACs 605, 607 can be connected to a bus device 610, or in some cases, the CDC 602. The circuitry can further include a microcontroller 612, which will be discussed in more detail below.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V.

Many different aspects can be calculated based on the capacitance data. For example, aspects that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different discrete graphene varactors and particularly between different discrete graphene varactors having specificity for different analytes.

Figure 7:
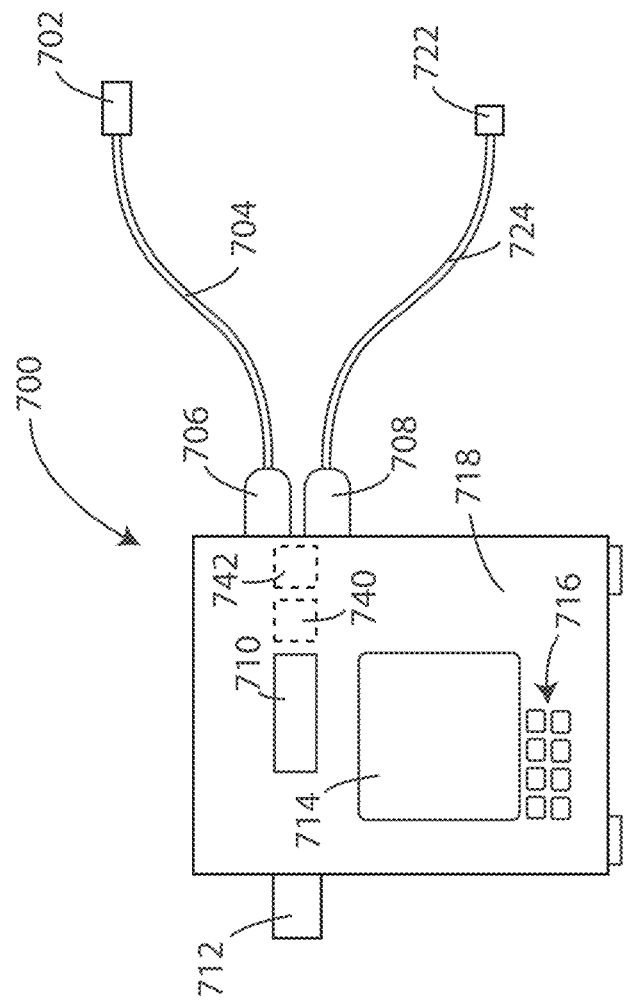
FIG. 7 is a schematic view of a system for sensing gaseous analytes in accordance with various embodiments herein.

Referring now to FIG. 7, a schematic view of a system 700 for sensing gaseous analytes in accordance with various embodiments herein is shown. The system 700 can include a housing 718. The system 700 can include a mouthpiece 702 into which a subject to be evaluated can blow a breath sample. The gaseous breath sample can pass through an inflow conduit 704 and pass through an evaluation sample (patient sample) input port 706. The system 700 can also include a control sample (environment) input port 708. The system 700 can also include a sensor element chamber 710, into which disposable sensor elements can be placed. The system 700 can also include a display screen 714 and a user input device 716, such as a keyboard. The system can also include a gas outflow port 712. The system 700 can also include flow sensors in fluid communication with the gas flow associated with one or more of the evaluation sample input port 706 and control sample input port 708. It will be appreciated that many different types of flow sensors can be used. In some embodiments, a hot-wire anemometer can be used to measure the flow of air. In some embodiments, the system can include a $CO_2$ sensor in fluid communication with the gas flow associated with one or more of the evaluation sample input port 706 and control sample input port 708.

In some embodiments, the evaluation sample input port 706 can be in fluid communication with the first measurement zone 304 and the gas flow pathway. In various embodiments, the control sample input port 708 can be in fluid communication with the second measurement zone 306 and the second gas flow pathway or the third measurement zone 308 and the third gas flow pathway.

In various embodiments, the system 700 can also include other functional components. By way of example, the system 700 can include a humidity control module 740 and/or a temperature control module 742. The humidity control module can be in fluid communication with the gas flow associated with one or more of the evaluation sample input port 706 and control sample input port 708 in order to adjust the humidity of one or both gas flow streams in order to make the relative humidity of the two streams substantially the same in order to prevent an adverse impact on the readings obtained by the system. The temperature control module can be in fluid communication with the gas flow associated with one or more of the evaluation sample input port 706 and control sample input port 708 in order to adjust the temperature of one or both gas flow streams in order to make the temperature of the two streams substantially the same in order to prevent an adverse impact on the readings obtained by the system. By way of example, the air flowing into the control sample input port can be brought up to 37 degrees Celsius or higher in order to match or exceed the temperature of air coming from a patient. The humidity control module and the temperature control module can be upstream from the input ports, within the input ports, or downstream from the input ports in the housing 718 of the system 700. In some embodiments, the humidity control module 740 and the temperature control module 742 can be integrated.

In some embodiments (not shown), the control sample input port 708 of system 700 can also be connected to an environmental sampling piece 722. In some embodiments, the environmental sampling piece 722 can include a switching airflow valve such that when the patient is drawing in breath, air flows from the control sample input port 708 into the system, and the system is configured so that this causes ambient air to flow across the appropriate control measurement zone (such as the second measurement zone). Then when the patient exhales, the switching airflow valve can switch so that a breath sample from the patient flows from the mouthpiece 702 through the environmental inflow conduit 724 and into the evaluation sample input port 706 and across the appropriate sample (patient sample) measurement zone (such as the first measurement zone 304) on the disposable sensor element. In other embodiments, the system can be configured to actively draw ambient air into the environmental sampling piece 722 such that this causes ambient air to flow across the appropriate control measurement zone (such as the second measurement zone).

In an embodiment, a method of making a chemical sensor element is included.

The method can include depositing one or more measurement zones onto a substrate. The method can further include depositing a plurality of discrete graphene varactors within the measurement zones on the substrate. The method can include generating one or more discrete graphene varactors by modifying a surface of a graphene layer with π-electron-rich molecules to form a self-assembled monolayer on an outer surface of the graphene layer through electrostatic interactions. The method can include quantifying the extent of surface coverage of the self-assembled monolayer using contact angle goniometry, Raman spectroscopy, or X-Ray photoelectron spectroscopy. The method can include selecting derivatized graphene layers that exhibit a Langmuir theta value of at least 0.9, as will be discussed more fully below. The method can further include depositing a component to store reference data onto the substrate. In some embodiments, the measurement zones can all be placed on the same side of the substrate. In other embodiments, the measurement zones can be placed onto different sides of the substrate.

In an embodiment, a method of assaying one or more gas samples is included. The method can include inserting a chemical sensor element into a sensing machine. The chemical sensor element can include a substrate and a first measurement zone 304 comprising a plurality of discrete graphene varactors. The first measurement zone 304 can define a portion of a first gas flow path. The chemical sensor element can further include a second measurement zone 306 separate from the first measurement zone 304. The second measurement zone 306 can also include a plurality of discrete graphene varactors. The second measurement zone 306 can be disposed outside of the first gas flow path. In various embodiments, the first measurement zone 304 can be in fluid communication with the evaluation sample input port 706 to define the first gas flow path, and the second measurement zone 306 is in fluid communication with the environmental sample input port 708 to define the second gas flow path separate from the first.

The method can further include prompting a subject to blow air into the sensing machine to follow the first gas flow path. In some embodiments, the $CO_2$ content of the air from the subject is monitored and sampling with the disposable sensor element is conducted during the plateau of $CO_2$ content, as it is believed that the air originating from the alveoli of the patient has the richest content of chemical compounds for analysis, such as volatile organic compounds. In some embodiments, the method can include monitoring the total mass flow of the breath sample and the control (or environmental) air sample using flow sensors. The method can further include interrogating the discrete graphene varactors to determine their analyte binding status. The method can further include discarding the disposable sensor element upon completion of sampling.

Figure 8:
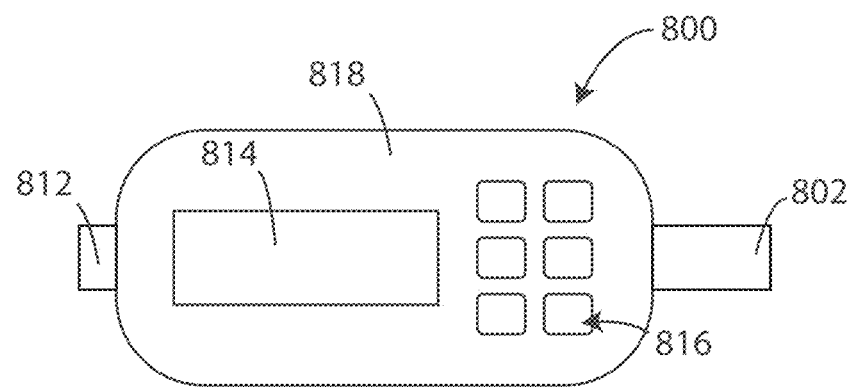
FIG. 8 is a schematic view of a system for sensing gaseous analytes in accordance with various embodiments herein.

Referring now to FIG. 8, a schematic view of a system 800 for sensing gaseous analytes in accordance with various embodiments herein is shown. In this embodiment, the system is in a hand-held format. The system 800 can include a housing 818. The system 800 can include a mouthpiece 802 into which a subject to be evaluated can blow a breath sample. The system 800 can also include a display screen 814 and a user input device 816, such as a keyboard. The system can also include a gas outflow port 812. The system can also include various other components such as those described with reference to FIG. 7 above.

In some embodiments, one of the measurement zones can be configured to indicate changes (or drift) in the chemical sensor element that could occur as a result of aging and exposure to varying conditions (such as heat exposure, light exposure, molecular oxygen exposure, humidity exposure, etc.) during storage and handling prior to use. In some embodiments, the third measurement zone can be configured for this purpose.

Figure 9:
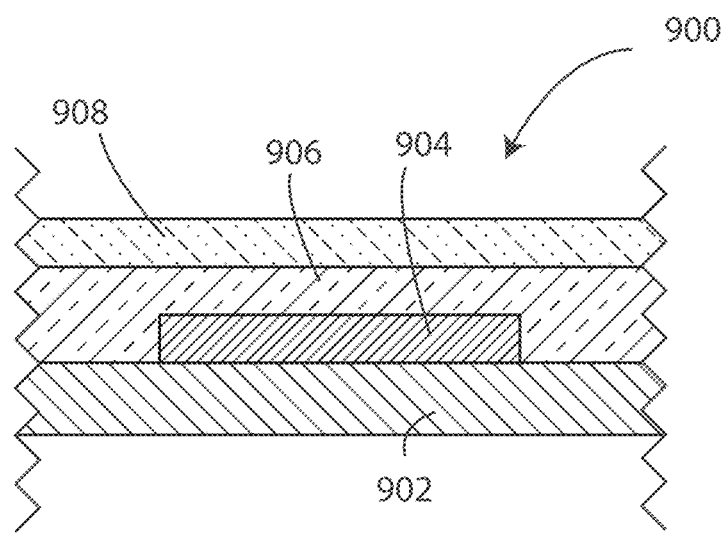
FIG. 9 is a schematic cross-sectional view of a portion of a chemical sensor element in accordance with various embodiments herein.

Referring now to FIG. 9, a schematic cross-sectional view is shown of a portion of a chemical sensor element 900 in accordance with various embodiments herein. The chemical sensor element 900 can include a substrate 902 and a discrete graphene varactor 904 disposed thereon that is part of a measurement zone. Optionally, in some embodiments the discrete graphene varactor 904 can be encapsulated by an inert material 906, such as nitrogen gas, or an inert liquid or solid. In this manner, the discrete graphene varactor 904 for the third measurement zone can be shielded from contact with gas samples and can therefore be used as a control or reference to specifically control for sensor drift which may occur between the time of manufacturing and the time of use of the disposable sensor element. In some embodiments, such as in the case of the use of an inert gas or liquid, the discrete binding detector can also include a barrier layer 908, which can be a layer of a polymeric material, a foil, or the like. In some cases, the barrier layer 908 can be removed just prior to use.

In an embodiment, method for detecting one or more analytes is included. The method can include collecting a gaseous sample from a patient. In some embodiments the gaseous sample can include exhaled breath. In other embodiments, the gaseous sample can include breath removed from the lungs of a patient via a catheter or other similar extraction device. In some embodiments, the extraction device can include an endoscope, a bronchoscope, or tracheoscope. The method can also include contacting a graphene varactor with the gaseous sample, where the graphene varactor includes a graphene layer and a self-assembled monolayer disposed on an outer surface of the graphene layer through electrostatic interactions. In some embodiments, the self-assembled monolayer can provide a Langmuir theta value of at least 0.9. Langmuir theta values will be discussed more fully below. In some embodiments, the method can include measuring a differential response in a capacitance of the graphene reactor due to the binding of one or more analytes present in the gaseous sample, which in turn can be used to identify disease states.

Graphene Varactors

The graphene varactors described herein can be used to sense one or more analytes in a gaseous sample, such as, for example, the breath of a patient. Graphene varactors embodied herein can exhibit a high sensitivity for volatile organic compounds (VOCs) found in gaseous samples at or near parts-per-million (ppm) or parts-per-billion (ppb) levels. The adsorption of VOCs onto the surface of graphene varactors can change the resistance, capacitance, or quantum capacitance of such devices, and can be used to detect the VOCs and/or patterns of binding by the same that, in turn, can be used to identify disease states such as cancer, cardiac diseases, infections, multiple sclerosis, Alzheimer's disease, Parkinson's disease, and the like. The graphene varactors can be used to detect individual analytes in gas mixtures, as well as patterns of responses in highly complex mixtures. In some embodiments, one or more graphene varactors can be included to detect the same analyte in a gaseous sample. In some embodiments, one or more graphene varactors can be included to detect different analytes in a gaseous sample. In some embodiments, one or more graphene varactors can be included to detect a multitude of analytes in a gaseous sample. In various embodiments, the one or more graphene varactors herein can be suitable for detecting one or more aldehyde compounds.

In some embodiments, the aldehyde compounds can include, but not be limited to, pentanal ($C_5H_{10}O$), hexanal ($C_6H_{12}O$), heptanal ($C_7H_{14}O$) octanal ($C_8H_{16}O$) and nonanal ($C_9H_{18}O$). In some embodiments, the ketone compounds can include, but not be limited to, acetone ($C_3H_6O$), 2-butanone ($C_4H_8O$), 2-pentanone ($C_5H_{10}O$), 3-pentanone ($C_5H_{10}O$), 2-hexanone ($C_6H_{12}O$), 3-hexanone ($C_6H_{12}O$), 2-heptanone ($C_7H_{14}O$), 3-heptanone ($C_7H_{14}O$), or 4-heptanone ($C_7H_{14}O$).

An exemplary graphene varactor can include a graphene layer and a self-assembled monolayer disposed on an outer surface of the graphene layer, interacting with the latter through electrostatic interactions, as shown and discussed above in reference to FIG. 2. The self-assembled monolayers suitable for use herein can provide a Langmuir theta value of at least 0.9. Determination of the Langmuir theta value for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98.

The graphene varactors described herein can include those in which a single graphene layer has been surface-modified through non-covalent electrostatic interactions with one or more compounds containing hydrazine or hydroxylamine functional groups, as described elsewhere herein. The compounds containing hydrazine or hydroxylamine functional groups described elsewhere herein, can include additional substitutions, including, but not to be limited to any number of functional groups described below, including, but not limited to alkyl groups, alkenyl groups, alkynyl, heteroalkyl groups, heteroalkenyl groups, and/or heteroalkynyl groups.

As used herein, the term "alkyl" refers to any linear or branched hydrocarbon functional group containing anywhere from 1 to 50 carbon atoms (i.e., $C_1$-$C_{50}$ alkyl). In some embodiments, the alkyl groups herein can contain any linear or branched hydrocarbon functional group containing anywhere from 6 to 32 carbon atoms (i.e., $C_6$-$C_{32}$ alkyl). In other embodiments, the alkyl groups herein can contain any linear or branched hydrocarbon functional group containing anywhere from 12 to 26 carbon atoms (i.e., $C_{12}$-$C_{26}$ alkyl). The alkyl groups described herein have the general formula $C_nH_{2n+1}$, unless otherwise indicated.

As used herein, the term "alkenyl" refers to any linear or branched hydrocarbon functional group containing anywhere from 1 to 50 carbon atoms, wherein the alkenyl group contains at least one carbon-carbon double bond (i.e., $C_1$-$C_{50}$ alkenyl). In some embodiments, the alkenyl groups herein can contain any linear or branched hydrocarbon functional group containing anywhere from 6 to 32 carbon atoms, wherein the alkenyl group contains at least one carbon-carbon double bond (i.e., $C_6$-$C_{32}$ alkenyl). In other embodiments, the alkyl groups herein can contain any linear or branched hydrocarbon functional group containing anywhere from 12 to 26 carbon atoms, wherein the alkenyl group contains at least one carbon-carbon double bond (i.e., $C_{12}$-$C_{26}$ alkenyl). The alkenyl groups described herein have the general formula $C_nH_{(2n+1-2x)}$, where x is the number of double bonds present in the alkenyl group, unless otherwise indicated.

As used herein, the term "alkynyl" refers to any linear or branched hydrocarbon functional group containing anywhere from 1 to 50 carbon atoms, including one or more carbon-carbon triple bonds (i.e., $C_1$-$C_{50}$ alkynyl). In some embodiments, the alkynyl groups herein can contain any linear or branched hydrocarbon functional group containing anywhere from 6 to 32 carbon atoms, including one or more carbon-carbon triple bonds (i.e., $C_6$-$C_{32}$ alkynyl). In other embodiments, the alkynyl groups herein can contain any linear or branched hydrocarbon functional group containing anywhere from 12 to 26 carbon atoms, including one or more carbon-carbon triple bonds (i.e., $C_{12}$-$C_{26}$ alkynyl).

As used herein, the term "heteroalkyl" refers to any linear or branched hydrocarbon functional group containing anywhere from 1 to 50 carbon atoms, and one or more heteroatoms, including, but not limited to, N, O, P, S, Si, Se, and B, or any combination thereof (i.e., $C_1$-$C_{50}$ heteroalkyl). In some embodiments, the heteroalkyl groups herein can contain any linear or branched hydrocarbon functional group containing anywhere from 6 to 32 carbon atoms and one or more heteroatoms, including, but not limited to, N, O, P, S, Si, Se, and B, or any combination thereof (i.e., $C_6$-$C_{32}$ heteroalkyl). In other embodiments, the heteroalkyl groups herein can contain any linear or branched hydrocarbon functional group containing anywhere from 12 to 26 carbon atoms and one or more heteroatoms, including, but not limited to, N, O, P, S, Si, Se, and B, or any combination thereof (i.e., $C_{12}$-$C_{26}$ heteroalkyl). In some embodiments, the heteroalkyl groups herein can have the general formula —RZR, —ZRZR, or —RZRZR, where R can include, but not be limited to, any identical or different, linear or branched, $C_1$-$C_{50}$ alkyl, or a combination thereof; and Z can include one or more heteroatoms including, but not limited to, N, O, P, S, Si, Se, and B, or any combination thereof.

In some embodiments, the heteroalkyl group can include, but not be limited to, alkoxy groups, alkyl amide groups, alkyl thioether groups, alkyl ester groups, and the like. Examples of heteroalkyl groups suitable for use herein can include, but not be limited to, those selected from —ROH, —RC(O)OH, —RC(O)OR, —ROR, —RSR, —RCHO, —RX, —RC(O) NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkyl, or a combination thereof; and X can be a halogen including F, Cl, Br, I, or At.

As used herein, the term "heteroalkenyl" refers to any linear or branched hydrocarbon functional group containing anywhere from 1 to 50 carbon atoms, including one or more carbon-carbon double bonds, and one or more heteroatoms including, but not limited to, N, O, P, S, Si, Se, and B, or any combination thereof (i.e., $C_1$-$C_{50}$ heteroalkenyl). In some embodiments, the heteroalkenyl groups herein can contain any linear or branched hydrocarbon functional group containing anywhere from 6 to 32 carbon atoms, including one or more carbon-carbon double bonds, and one or more heteroatoms, including, but not limited to, N, O, P, S, Si, Se, and B, or any combination thereof (i.e., $C_6$-$C_{32}$ heteroalkenyl). In other embodiments, the heteroalkenyl groups herein can contain any linear or branched hydrocarbon functional group containing anywhere from 12 to 26 carbon atoms, including one or more carbon-carbon double bonds, and one or more heteroatoms, including, but not limited to, N, O, P, S, Si, Se, and B, or any combination thereof (i.e., $C_{12}$-$C_{26}$ heteroalkenyl). In some embodiments, the heteroalkenyl groups herein can have the general formula —RZR, —ZRZR, or —RZRZR, where R can include, but not be limited to, any identical or different, linear or branched, $C_1$-$C_{50}$ alkyl or $C_1$-$C_{50}$ alkenyl, provided that at least one carbon-carbon double bond is present in at least one R group, or a combination thereof; and Z can include one or more heteroatoms including, but not limited to, N, O, P, S, Si, Se, and B, or any combination thereof.

In some embodiments, the heteroalkenyl group can include, but not limited to, alkenoxy groups, alkenyl amines, alkenyl thioester groups, alkenyl ester groups, and the like. Examples of heteroalkenyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkenyl, or a combination thereof; and X can be a halogen including F, Cl, Br, I, or At.

As used herein, the term "heteroalkynyl" refers to any linear or branched hydrocarbon functional group containing anywhere from 1 to 50 carbon atoms, including one or more carbon-carbon triple bonds, and one or more heteroatoms including, but not limited to, N, O, P, S, Si, Se, and B, or any combination thereof (i.e., $C_1$-$C_{50}$ heteroalkynyl). In some embodiments, the heteroalkynyl groups herein can contain any linear or branched hydrocarbon functional group containing anywhere from 6 to 32 carbon atoms, including one or more carbon-carbon triple bonds, and one or more heteroatoms, including, but not limited to, N, O, P, S, Si, Se, and B, or any combination thereof (i.e., $C_6$-$C_{32}$ heteroalkynyl). In other embodiments, the heteroalkynyl groups herein can contain any linear or branched hydrocarbon functional group containing anywhere from 12 to 26 carbon atoms, including one or more carbon-carbon triple bonds, and one or more heteroatoms, including, but not limited to, N, O, P, S, Si, Se, and B, or any combination thereof (i.e., $C_{12}$-$C_{26}$ heteroalkynyl). In some embodiments, the heteroalkynyl groups herein can have the general formula —RZR, —ZRZR, or —RZRZR, where R can include, but not be limited to, any identical or different, linear or branched, $C_1$-$C_{50}$ alkyl, $C_1$-$C_{50}$ alkenyl, or $C_1$-$C_{50}$ alkynyl, provided that at least one carbon-carbon triple bond is present in at least one R group or a combination thereof; and Z can include one or more heteroatoms including, but not limited to, N, O, P, S, Si, Se, and B, or any combination thereof.

In some embodiments, the heteroalkynyl group can include, but not limited to, alkynyloxy groups, alkynyl amines, alkynyl thioester groups, alkynyl ester groups, and the like. Examples of heteroalkynyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkynyl, or a combination thereof; and X can be a halogen including F, Cl, Br, I, or At.

In some embodiments, the compounds suitable for the self-assembled monolayers described herein can include sensing molecules having the general formula (1):

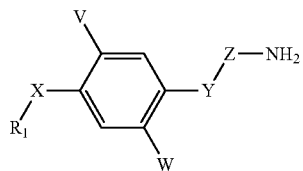

and any tautomers thereof; where Z includes NH or O; where $R^1$ includes $(CH_2)_mCH_3$ and 50>m>5; where X includes $CH_2$, O, NH, $N(CH_2)_nCH_3$, —C(=O)O—, —OC(=O)—, —C(=O)NH—, —NHC(=O)—, —C(=O)N$((CH_2)_nCH_3)$—, —N$((CH_2)_nCH_3)$C(=O)—, —S, —S(=O)—, —S(=O)$_2$—, —S(=O)$_2$O—, —OS(=O)$_2$—, —S(=O)$_2$NH—, —NHS(=O)$_2$—, —S(=O)$_2$N$((CH_2)_nCH_3)$—, —N$((CH_2)_nCH_3)$S(=O)$_2$— and n is 0, or 1 to 20; where Y includes $(C_6H_4)_p$ or $(CH_2)_p$ and p is 0, 1, or 2; where W includes H, $(CH_2)_qOH$, $(CH_2)_qCOOH$, $(CH_2)_qSO_2OH$, or $(CH_2)_qPO_2OH$, and q is 0, 1, or 2;

where V includes H, NO, NO$_2$, Cl, Br, I, F, CF$_3$, —CN, —NC, $C_6H_5$ (phenyl), OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$^2$S(=O)$_2$R, and where R and $R^2$ comprise $(CH_2)_kCH_3$ and k is 0, 1, or 2; and where $R^1$X and V can be present in any ring position relative to a YZNH$_2$ group and W is present in an alpha position relative to the YZNH$_2$ to provide proximity between W and YZNH$_2$. It will be appreciated that when W is present in an alpha position relative to the YZNH$_2$ the positioning is effective to permit interaction of an acidic hydrogen on W and an incoming aldehyde oxygen atom. The configuration of W in the alpha position to YZNH$_2$ is configured to be effective to permit interaction of an acidic hydrogen atom on W with an aldehyde molecule so as to catalyze a reaction of the aldehyde with the hydrazine or hydroxylamine group. In various embodiments, the self-assembled monolayer further includes an acidic compound effective to catalyze a reaction between the hydrazine groups or hydroxylamine groups and an aldehyde or ketone.

In other embodiments, protonation of the NH$_2$ group on the hydrazine or hydroxylamine group, or the NH group, when Z is NH, will yield an NH$_3^+$ or NH$_2^+$, respectively, to attract anionic groups to balance electroneutrality. In addition, the V moiety can include one or more electron-donating or withdrawing groups that control the electron density and thus influence the activity of the YZNH$_2$ group. In various embodiments, the compounds herein can include one or more $R^1$X groups to be utilized in self-assembly with graphene. In various embodiments, the formula comprises more than one $R^1$X moiety effective to induce self-assembly of the compound.

In some embodiments, the compounds suitable for the self-assembled monolayers described herein can include sensing molecules having the general formula (2):

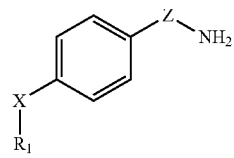

where Z includes NH or O; where $R^1$ includes $(CH_2)_mCH_3$ and $50>m>5$; and where X includes $CH_2$, O, NH, $N(CH_2)_nCH_3$, —C(=O)O—, —OC(=O)—, —C(=O)NH—, —NHC(=O)—, —C(=O)N(($CH_2)_nCH_3$)—, —N(($CH_2)_nCH_3$)C(=O)—, —S—, —S(=O)—, —S(=O)$_2$—, —S(=O)$_2$O—, —OS(=O)$_2$—, —S(=O)$_2$NH—, —NHS(=O)$_2$—, —S(=O)$_2$N(($CH_2)_nCH_3$)—, —(($CH_2)_nCH_3$)S(=O)$_2$— and n is 0, or 1 to 20.

In various embodiments, the self-assembled monolayer described herein includes the sensing molecule 4-hexadecylphenylhydrazine having the formula (3):

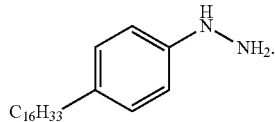

In some embodiments, the compounds suitable for the self-assembled monolayers described herein can include sensing molecules having the general formula (4):

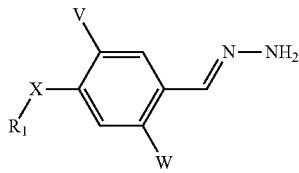

and any tautomers thereof; where $R^1$ includes $(CH_2)_mCH_3$, where $50>m>5$; where X includes $CH_2$, O, NH, $N(CH_2)_nCH_3$, —C(=O)O—, —OC(=O)—, —C(=O)NH—, —NHC(=O)—, —C(=O)N(($CH_2)_nCH_3$)—, —N(($CH_2)_nCH_3$)C(=O)—, —S—, —S(=O)—, —S(=O)$_2$—, —S(=O)$_2$O—, —OS(=O)$_2$—, —S(=O)$_2$NH—, —NHS(=O)$_2$—, —S(=O)$_2$N(($CH_2)_nCH_3$)—, —N(($CH_2)_nCH_3$)S(=O)$_2$—, and n is 0, or 1 to 20;

where W includes H, $(CH_2)_qOH$, $(CH_2)_qCOOH$, $(CH_2)_qSO_2OH$, or $(CH_2)_qPO_2OH$, and q is 0, 1, or 2;

wherein V includes H, NO, $NO_2$, Cl, Br, I, F, $CF_3$, —CN, —NC, $C_6H_5$ (phenyl), OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$^2$S(=O)$_2$R, and where R and $R^2$ include $(CH_2)_kCH_3$ and k is 0, 1, or 2; and where $R^1$X and V can be present in any ring position relative to an $NNH_2$ group and W is present in an alpha position relative to the $NNH_2$ group. It will be appreciated that when W is present in an alpha position relative to the $NNH_2$ group the positioning is effective to permit interaction of an acidic hydrogen on W and an incoming aldehyde oxygen atom. The configuration of W in the alpha position to $YZNH_2$ is configured to be effective to permit interaction of an acidic hydrogen atom on W with an aldehyde molecule so as to catalyze a reaction of the aldehyde with the hydrazine or hydroxylamine group. In various embodiments, the self-assembled monolayer further includes an acidic compound effective to catalyze a reaction between the hydrazine groups or hydroxylamine groups and an aldehyde or ketone. In addition, the V moiety can include one or more electron-donating or withdrawing groups that control the electron density and thus influence the activity of the $NNH_2$ group. In various embodiments, the compounds herein can include one or more $R^1X$ groups to be utilized in self-assembly with graphene. In various embodiments, the formula comprises more than one $R^1X$ moiety effective to induce self-assembly of the compound.

In some embodiments, the compounds suitable for the self-assembled monolayers described herein can include sensing molecules having the general formula (5):

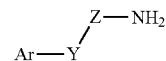

and any tautomers thereof; where Z includes NH or O; where Y includes $(CH_2)_p$ and p is from 0 to 20; and where Ar comprises an aromatic substituent with 16 or more aromatic carbons. The aromatic substituent can include, but not be limited to, naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof. The aromatic substituent further comprise substitutions including $(CH_2)_qOH$, $(CH_2)_qCOOH$, $(CH_2)_qSO_2OH$, or $(CH_2)_qPO_2OH$ where q is 0, 1, or 2, in a position alpha to a $YZNH_2$ group effective to permit interaction of an acidic hydrogen atom on the substitution with an aldehyde molecule. In various embodiments, Ar comprises aromatic substituent with 16 or more aromatic carbons having one or more substitutions, where the one or more substitutions can include H, OH, a halogen, $NO_2$, COOH, $SO_3H$, $PO_3H$, $NH_2$, CN, O—$NH_2$, S—$NH_2$, N—$NH_2$, OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$^2$S(=O)$_2$R, and where R and $R^2$ are alkyl, alkenyl, alkynyl, heteroalkyl, heteroalkenyl, heteroalkynyl, halogenated alkyl, halogenated heteroalkyl, halogenated alkenyl, halogenated heteroalkenyl, halogenated alkynyl, or halogenated heteroalkynyl, as described elsewhere herein.

In some embodiments, the compounds suitable for the self-assembled monolayers described herein can include sensing molecules having the general formula (6):

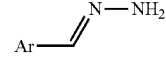

and any tautomers thereof, where Ar comprises an aromatic substituent with 16 or more aromatic carbons. The aromatic substituent can include, but not be limited to, naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof. The aromatic substituent further comprises substitutions including $(CH_2)_qOH$, $(CH_2)_qCOOH$, $(CH_2)_qSO_2OH$, or $(CH_2)_qPO_2OH$ where q is 0, 1, or 2, in a position alpha to a $NNH_2$ group effective to permit interaction of an acidic hydrogen atom on the substitution with an aldehyde molecule. In various embodiments, Ar comprises aromatic substituent with 16 or more aromatic carbons having one or more substitutions, where the one or more substitutions can include H, OH, a halogen, $NO_2$, COOH, $SO_3H$, POSH, $NH_2$, CN, O—$NH_2$, S—$NH_2$, N—$NH_2$, OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)

$_2NRR^2$, $-NR^2S(=O)_2R$, and where R and $R^2$ are alkyl, alkenyl, alkynyl, heteroalkyl, heteroalkenyl, heteroalkynyl, halogenated alkyl, halogenated heteroalkyl, halogenated alkenyl, halogenated heteroalkenyl, halogenated alkynyl, or halogenated heteroalkynyl, as described elsewhere herein.

Embodiments herein specifically include any of the compounds suitable for the self-assembled monolayers as described herein. That is, embodiments herein include the compounds themselves, even when not a part of a self-assembling monolayer on a layer of graphene. Thus, in various embodiments, a compound for modifying a graphene layer is included, wherein the compound comprises any of the compounds described herein to be suitable for formation of a self-assembling monolayer on a graphene surface. In an embodiment, a compound for modifying a graphene layer is included, the compound comprising any of formulas 1, 2, 3, 4, 5, or 6 as described above.

Contact Angle Goniometry

Contact angle goniometry can be used to determine the wettability of a solid surface by a liquid. Wettability, or wetting, can result from the intermolecular forces at the contact area between a liquid and a solid surface. The degree of wetting can be described by the value of the contact angle Φ formed between the area of contact between the liquid and the solid surface and a line tangent to the liquid-vapor interface. When a surface of a solid is hydrophilic and water is used as the test liquid, (i.e., a high degree of wettability), the value for Φ can fall within a range of 0 to 90 degrees. When a surface of a solid is moderately hydrophilic to hydrophobic, (i.e., a medium degree of wettability), the value for Φ for water as the test liquid can fall within a range of 85 to 105 degrees. When the surface of a solid is highly hydrophobic, (i.e., a low degree of wettability), the value for Φ with water as the test liquid can fall within a range of 90 to 180 degrees. Thus, a change in contact angle can be reflective of a change in the surface chemistry of a substrate.

Graphene surfaces and modifications made to graphene surfaces can be characterized using contact angle goniometry. Contact angle goniometry can provide quantitative information regarding the degree of modification of the graphene surface.

Contact angle measurements are highly sensitive to the functional groups present on sample surfaces and can be used to determine the formation and extent of surface coverage of self-assembled monolayers. A change in the contact angle from a bare graphene surface as compared to one that has been immersed into a self-assembly solution containing π-electron-rich molecules, can be used to confirm the formation of the self-assembled monolayer on the surface of the graphene.

The types of solvents suitable for use in determining contact angle measurements, also called wetting solutions, are those that maximize the difference between the contact angle of the solution on bare graphene and the contact angle on the modified graphene, thereby improving data accuracy for measurements of binding isotherms. In some embodiments, the wetting solutions can include, but are not limited to, deionized (DI) water, NaOH aqueous solution, borate buffer (pH 9.0), other pH buffers, trifluoroethanol ($CF_3CH_2OH$), and the like. In some embodiments, the wetting solutions are polar. In some embodiments, the wetting solutions are non-polar.

Langmuir Adsorption Theory

Without wishing to be bound by any particular theory, it is believed that according to Langmuir adsorption theory, monolayer modification of graphene can be controlled by varying the concentration of the adsorbate in the bulk of the self-assembly solution according to:

$$\theta = \frac{K*C}{1+K*C} \quad (1)$$

where θ is the fractional surface coverage, C is the concentration of the adsorbate in the bulk of the self-assembly solution, and K is the equilibrium constant for adsorption of the adsorbate to graphene. Experimentally, the surface coverage can be expressed by the change in contact angle between bare graphene and modified graphene according to:

$$\theta = \frac{\Phi(i) - \Phi(\text{bare})}{\Phi(\text{sat.}) - \Phi(\text{bare})} \quad (2)$$

where Φ(i) is the contact angle of the modified graphene as a function of the concentration in the self-assembly solution, Φ(bare) is the contact angle of bare graphene, and Φ(sat.) is the contact angle of graphene modified with a complete monolayer of receptor molecules (i.e., 100% surface coverage or θ=1.0). Insertion of θ from eq. (2) into eq. (1) and solving for Φ(i) gives eq. (3)

$$\Phi(i) = \Phi(\text{bare}) + \frac{K*C\ [\Phi(\text{sat.}) - \Phi(\text{bare})]}{1+K*C} \quad (3)$$

Thus, the experimentally observed Φ(i) values can be fitted as a function of receptor concentration in the self-assembly solution, using the two fitting parameters K and Φ(sat.). Once these two parameters have been determined, relative surface coverages at different self-assembly concentrations can be predicted from eq. (1), using K.

Data can be fitted with the Langmuir adsorption model to determine the equilibrium constants for surface adsorption and the concentrations of self-assembly solutions needed to form dense monolayers having 90% or greater surface coverage (i.e., θ>0.9) on graphene. In some embodiments, a surface coverage of at least 90% or greater is desired. In some embodiments, a surface coverage of at least 95% or greater is desired. In some embodiments, a surface coverage of at least 98% or greater is desired.

X-Ray Photoelectron Spectroscopy

X-ray photoelectron spectroscopy (XPS) is a highly sensitive spectroscopic technique that can quantitatively measure the elemental composition of a surface of a material. The process of XPS involves irradiation of a surface with X-rays under a vacuum, while measuring the kinetic energy and electron release within the top 0 to 10 nm of a material. Without wishing to be bound by any particular theory, it is believed that XPS can be used to confirm the presence of a self-assembled monolayer formed on the surface of graphene.

The surface concentrations of the types of atoms that the monolayer, graphene, and the underlying substrate consist of (as determined from XPS) depends on the Langmuir theta value of the monolayer or, in other words, the surface density of the monolayer molecules on the graphene. For example, the surface concentrations of carbon, oxygen, and copper (i.e., C %, O %, and Cu %, as determined from XPS) for the monolayers of any given 4-alkylphenylhydrazine on a graphene coated copper substrate depends on the concentration of that 4-hexadecylphenylhydrazine in the self-assembly solution. Due to experimental error, a slightly different value of the equilibrium constant, K, for surface adsorption will result when either the C %, O %, or Cu % data are fitted separately. However, because the C %, O %, or Cu % data characterize the same equilibrium, there is only one true value for K. Therefore, the XPS data can not only be fitted separately for the C %, O %, and Cu % data but also as one combined set of data. Fitting of the combined data for several types of atoms that the monolayer, graphene, and the underlying substrate consist of gives more accurate estimates of the true value of K. For this purpose, the following equation can be used, where each data point consists of a vector comprising (i) an index, (ii) the concentration of the self-assembly solution, and (iii) the carbon, oxygen, or copper concentration as determined by XPS.

$$KroneckerDelta[1-\text{index}]*$$
$$\left\{ C\ \%(\text{bare}) + \frac{K*Conc*[C\ \%(\text{sat.}) - C\ \%(\text{bare})]}{1 + K*Conc} \right\} +$$
$$KroneckerDelta[2-\text{index}]*$$
$$\left\{ O\ \%(\text{bare}) + \frac{K*Conc*[O\ \%(\text{sat.}) - O\ \%(\text{bare})]}{1 + K*Conc} \right\} +$$
$$KroneckerDelta[3-\text{index}]*$$
$$\left\{ Cu\ \%(\text{bare}) + \frac{K*Conc*[Cu\ \%(\text{sat.}) - Cu\ \%(\text{bare})]}{1 + K*Conc} \right\}$$

The index 1 was used for the C % data, 2 for the O % data, and 3 for the Cu % data. The output of the Kronecker delta for the input of 0 is 1, and it is 0 for any other input. This fitting procedure provides in one step the maximum surface concentrations of carbon, oxygen, and copper (i.e., C % (sat.), O % (sat.), and Cu % (sat.), respectively) along with one single value for K for all three adsorption isotherms.

In the example above, the K value is fitted from 3 adsorption isotherms, that is, the surface concentrations of 3 types of atoms. The same type of fit may also be performed for adsorption isotherms of 1, 2, 3, 4, 5, 6, 7, 8, 9, 10, or more different types of atoms.

The equilibrium constant K, as determined by the fit of the XPS data, can be used in the Langmuir adsorption model to determine the θ value for graphene surfaces modified with various molecules forming monolayers on graphene, such as compounds containing hydrazine or hydroxylamine functional groups, and their tautomers and derivatives.

Methods

The embodiments herein include methods for modifying the surface of graphene. In an embodiment, the method can include modifying a surface of graphene to create a graphene varactor including forming a self-assembled monolayer disposed on an outer surface of the graphene layer through electrostatic interactions between a partial positive charge on hydrogen atoms of more hydrocarbons of the self-assembled monolayer and a π-electron system of graphene. The self-assembled monolayer can include one or more compounds comprising hydrazine or hydroxylamine groups, substituted hydrazine or hydroxylamine groups, or derivatives thereof. In some embodiments, the method can include quantifying the extent of surface coverage of the self-assembled monolayer using contact angle goniometry, Raman spectroscopy, or x-ray photoelectron spectroscopy. In various embodiments, the method can include selecting derivatized graphene layers that exhibit a Langmuir theta value of at least 0.9. In other embodiments, the method can include selecting derivatized graphene layers that exhibit a Langmuir theta value of at least 0.98.

In various embodiments, the methods herein can include detecting an analyte by collecting a gaseous sample from a patient and contacting the gaseous sample with one or more graphene varactors. The one or more graphene varactors include a graphene layer and a self-assembled monolayer disposed on an outer surface of the graphene layer through electrostatic interactions between a partial positive charge on hydrogen atoms of more hydrocarbons of the self-assembled monolayer and a π-electron system of graphene. The self-assembled monolayer can include at least one selected from the group including compounds comprising hydrazine or hydroxylamine groups, substituted hydrazine or hydroxylamine groups, or derivatives thereof. The method further can include measuring a differential response in an electrical property of the one or more graphene varactors due to the binding of one or more analytes present in the gaseous sample, where the electrical property is selected from the group including capacitance or resistance. In various embodiments, the self-assembled monolayer provides a Langmuir theta value of at least 0.98. In other embodiments, the self-assembled monolayer provides a Langmuir theta value of at least 0.9.

Aspects may be better understood with reference to the following examples. These examples are intended to be representative of specific embodiments, but are not intended as limiting the overall scope of embodiments herein.

EXAMPLES

Example 1: Materials

Aniline, O-phenylhydroxylamine hydrochloride, phenylhydrazine, benzaldehyde, tetrahydrofuran-$d_8$ (THF-$d_8$), and trifluoroacetic acid (TFA) were purchased from Sigma Aldrich. Deionized water (DI water, 0.18 MΩ m specific resistance) was obtained by purification with a Milli-Q PLUS reagent-grade water system (Millipore, Billerica, MA). Cyclohexane (15 millimolar (mM), unless otherwise stated) was used as an internal standard. All self-assembly compounds were assessed by $^1$H NMR spectroscopy at a 1.1 molar equivalent, from 15-25 mM.

Example 2: Preparation of Reagents

O-phenylhydroxylamine hydrochloride was neutralized prior to use in $^1$H NMR studies. To a suspension of O-phenylhydroxylamine hydrochloride in water, a 1 M aqueous sodium bicarbonate solution was added dropwise until the formation of bubbles ceased. The aqueous solution was then extracted three times with dichloromethane. The organic layer was dried with magnesium sulfate and the solvent was evaporated under a stream of nitrogen, leaving a brown oil of O-phenylhydroxylamine. $^1$H NMR confirmed the identity of the desired product. All other reagents were used as purchased.

Example 3: $^1$H NMR Spectroscopy Methods

A THF-$d_8$ solvent stock solution was made to contain $H_2O$ (5% v/v) and TFA (5 mol %) relative the concentration of the probe used) and 15 mM cyclohexane as an internal standard. Aniline (30 mM), phenylhydrazine (40 mM), and O-phenylhydroxylamine (116 mM) probe solutions and a benzaldehyde (30 mM) solution were prepared with the THF-$d_8$ stock solution. Immediately before measuring NMR spectra, 300 μL of probe solution and 300 μL of benzaldehyde solution were added to an NMR tube with a syringe, which was then inverted twice to mix. ¹H NMR spectra were recorded at different time intervals. Reference spectra of benzaldehyde, phenylhydrazine, O-phenylhydroxylamine, and aniline were prepared by mixing 300 μL of each solution with 300 μL of the solvent stock solution. All ¹H NMR experiments were performed on a Bruker Advance III (500 MHz).

Example 4: Comparative Example of Condensation of Aniline Reported by ¹H NMR Spectroscopy The condensation reaction of aniline and benzaldehyde forms an imine product as shown in the following reaction scheme:

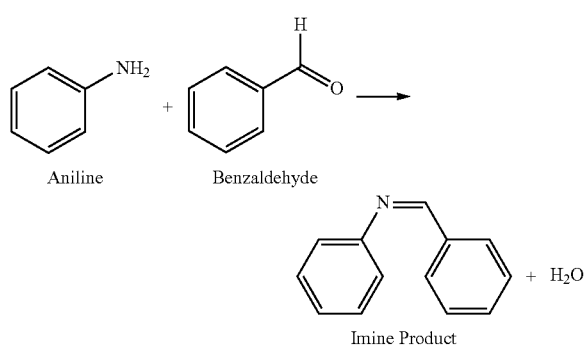

Figure 10:
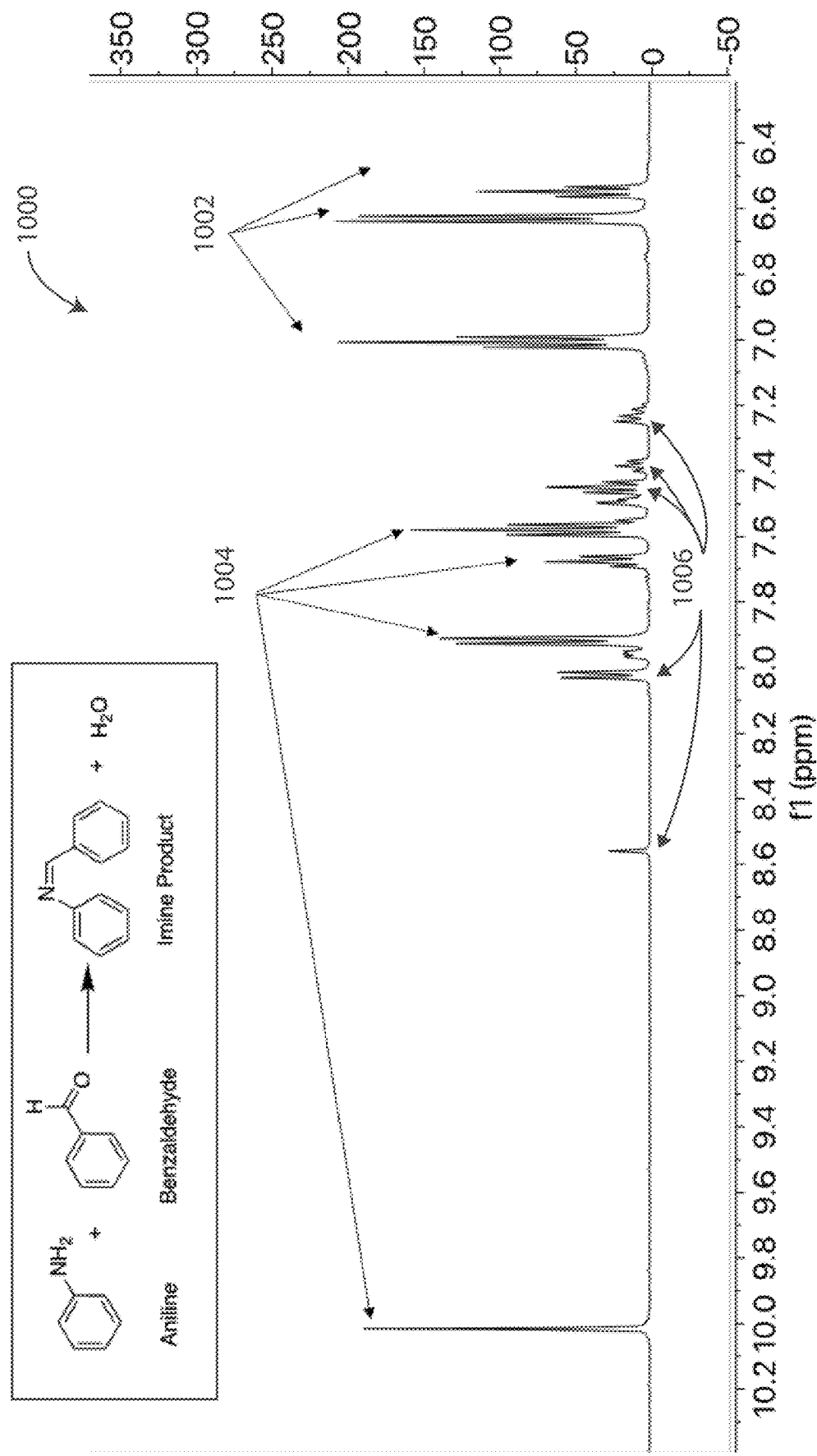
FIG. 10 is a representative $^1$H NMR spectrum of an exemplary reaction in accordance with various embodiments herein.
Figure 11:
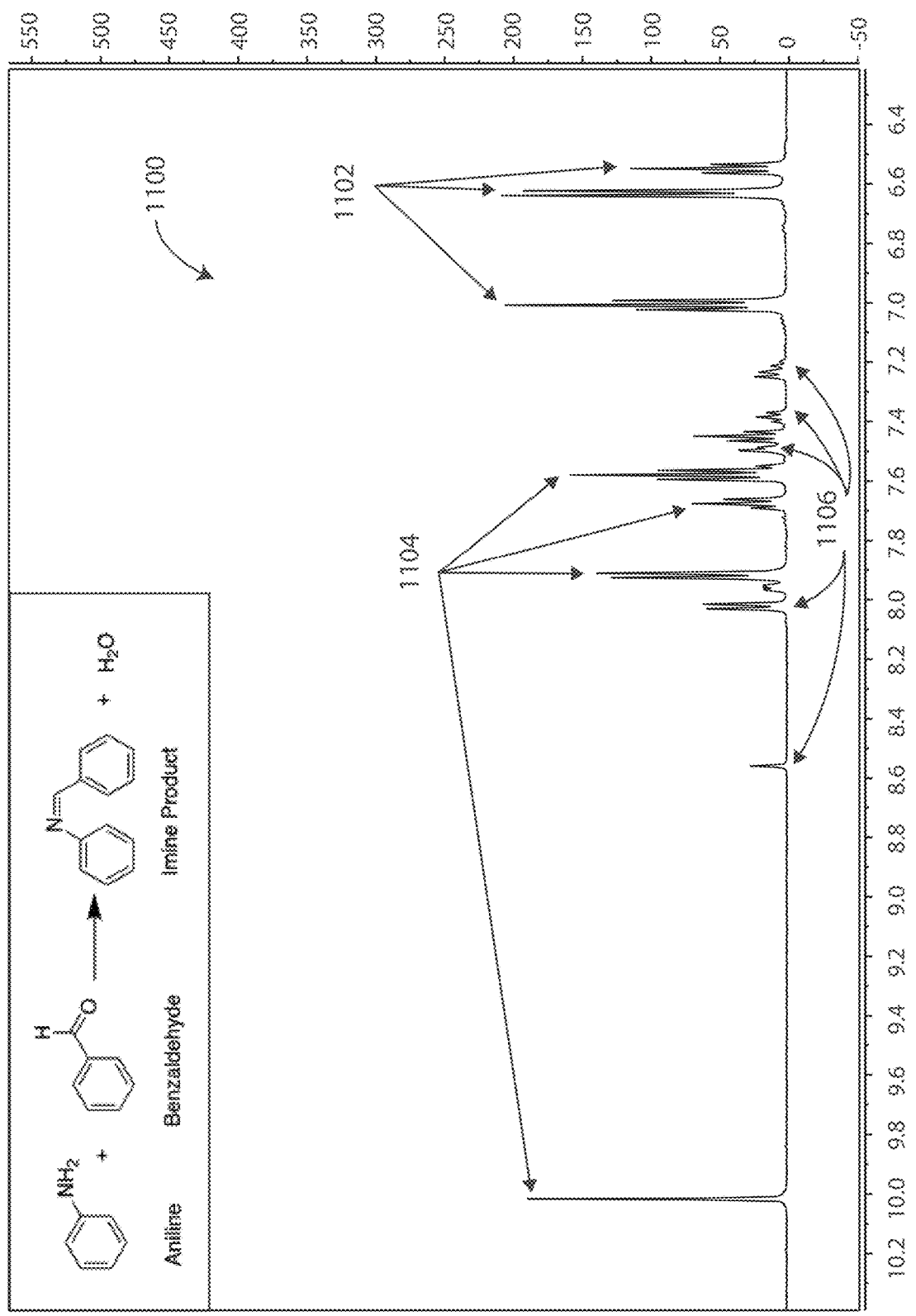
FIG. 11 is a representative $^1$H NMR spectrum of an exemplary reaction in accordance with various embodiments herein.

A reaction mixture of aniline/benzaldehyde (1.1:1 molar equivalents) was prepared, and ¹H NMR (500 MHz) spectra were recorded every five minutes for a total of 40 minutes. The ¹H NMR spectra 1100 of aniline/benzaldehyde (1.1:1 molar equivalents) reaction (THF-d₈, 5% v/v H₂O, 5 mol % THF) were obtained at 2 hours (FIG. 10) and at 24 hours (FIG. 11). After 2 hours, the ¹H NMR spectrum 1000 reveals that the reaction of aniline and benzaldehyde under the specified conditions favors the reactants aniline and benzaldehyde, as evidenced by the ¹H NMR peaks corresponding to aniline 1002, benzaldehyde 1004. A minor amount of the imine product 1006 is also present, as shown in FIG. 10. After 24 hours, the ¹H NMR spectrum 1000 reveals that the reaction of aniline and benzaldehyde under the specified conditions continues to favor the reactants aniline and benzaldehyde. As shown in FIG. 11 the ¹H NMR peaks corresponding to aniline 1102, benzaldehyde 1104, and imine product 1106 reveal little to not change as compared to the reaction after 2 hours. The data presented in FIG. 10 and FIG. 11 suggests that aniline-based compounds, while suitable for use in some analytical devices for the measurement of aldehydes, the aniline-based compounds reveal an incomplete and slow reaction with benzaldehyde over 24 hours in comparison other hydrazine and hydroxylamine compounds analyzed herein.

Example 5: Condensation of O-phenylhydroxylamine Reported by ¹H NMR Spectroscopy The condensation reaction of O-phenylhydroxylamine and benzaldehyde forms an oxime product as shown:

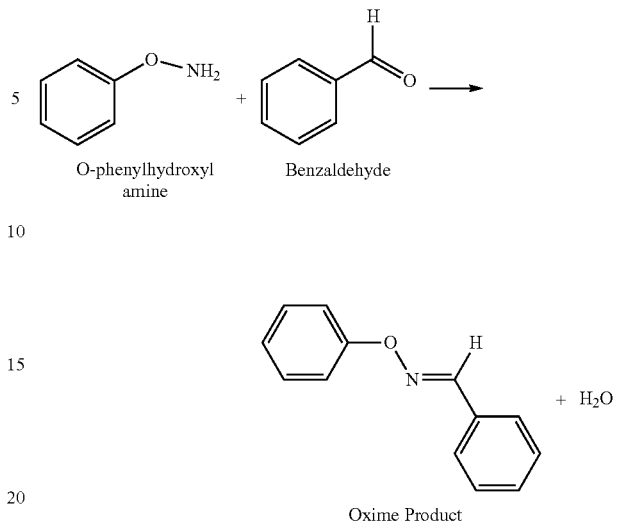

A reaction mixture of 58 mM O-phenylhydroxylamine and 26 mM benzaldehyde was prepared, and ¹H NMR spectra were recorded every five minutes for a total of 40 minutes. A series of ¹H NMR spectra 1200 of the aromatic region (500 MHz) of the O-phenylhydroxyamine/benzaldehyde (2:1 molar equivalents) reaction were obtained in THF-d₈ with 15 mM cyclohexane internal standard, 5 mol % TFA and 5% v/v H₂O is shown in FIG. 12.

Figure 12:
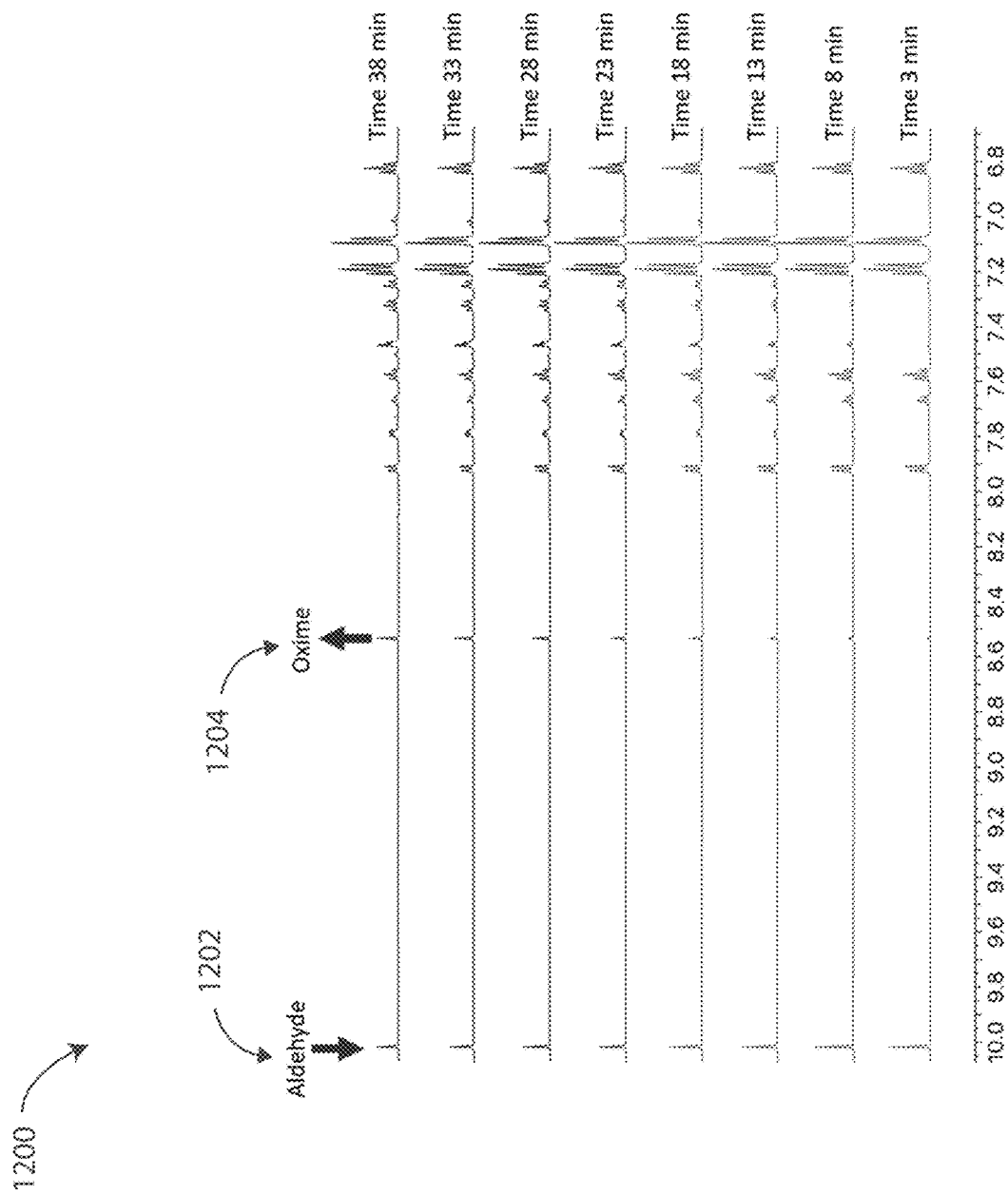
FIG. 12 is a series of $^1$H NMR spectra of exemplary reaction in accordance with various embodiments herein.

As shown in FIG. 12, the HCO peak 1202 of benzaldehyde at 10.2 ppm shows a decline over the span of 40 minutes when a 2:1 ratio (molar equivalents) of the reactants O-phenylhydroxylamine to benzaldehyde was used. At the same time, the HCN peak 1204 of the oxime at 8.5 ppm shows an increase over the span of 40 minutes when a 2:1 ratio (molar equivalents) of the reactants O-phenylhydroxylamine to benzaldehyde was used. The decline of benzaldehyde from 3 minutes (bottom) to 38 minutes (top) indicates the conversion of the reactants into the oxime product. The increase of oxime product from 3 minutes (bottom) to 38 minutes (top) further indicates the conversion of the reactants into the oxime product. The results show peak overlap and splitting patters in the oxime product peaks that are indicative of the reaction producing a mixture of E and Z isomers. After 24 hours O-phenylhydroxylamine and benzaldehyde reactants remained in the system indicating that equilibrium was not yet met.

Figure 13:
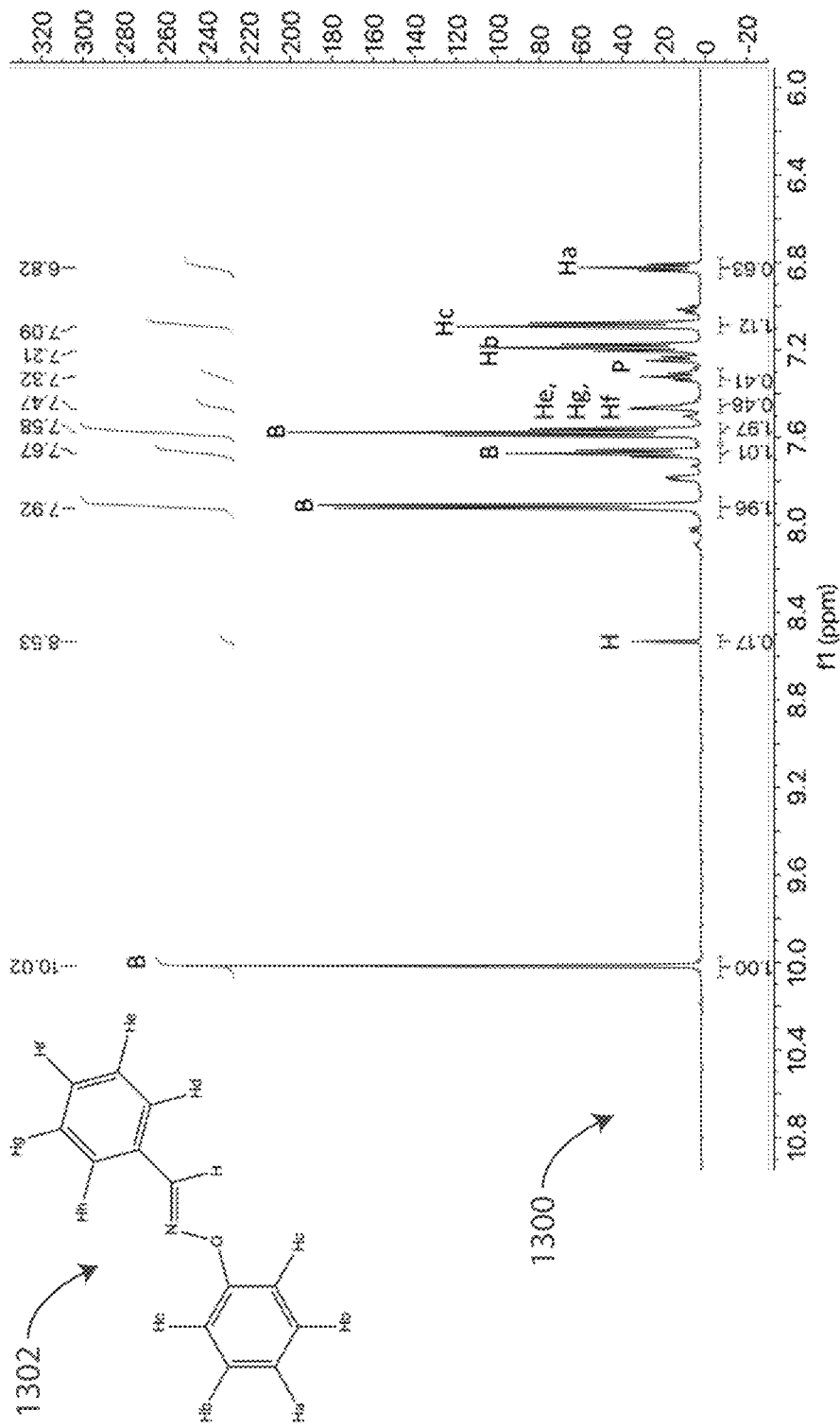
FIG. 13 is a representative $^1$H NMR spectrum of exemplary compound in accordance with various embodiments herein.

A ¹H NMR spectrum 1300 with various oxime product peaks labelled is shown in FIG. 13. The ¹H NMR spectrum (500 MHz) of the O-phenylhydroxylamine/benzaldehyde (1:1.1 molar equivalents) reaction (THF-d₈, 5% v/v H₂O, 5 mol % THF) of FIG. 13 was obtained at 20 minutes. Peak labels correspond to the labeled oxime product structure (inlay 1302), where respective hydrogen atoms are labeled H, $H_a$, $H_b$, $H_c$, $H_d$, $H_e$, $H_f$, $H_g$, and $H_h$. Additional peaks labelled B and P correspond to the unreacted benzaldehyde and O-phenylhydroxylamine, respectively.

Example 6: Condensation of Phenylhydrazine Reported by ¹H NMR Spectroscopy

The condensation reaction of phenylhydrazine and benzaldehyde forms a hydrazone product as shown:

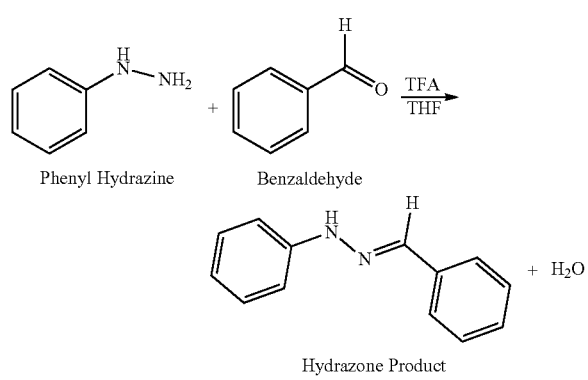

Phenyl Hydrazine  Benzaldehyde

Hydrazone Product

A reaction mixture of 23 mM phenylhydrazine and 17 mM benzaldehyde was prepared, and ¹H NMR spectra were recorded every five minutes for a total of 35 minutes. A series ¹H NMR spectra 1400 (500 MHz) of the phenylhydrazine/benzaldehyde (1.4:1 molar equivalents) reaction in THF-d$_8$ with 15 mM cyclohexane internal standard, 5 mol % TFA and 5 vol % H$_2$O is shown in FIG. 14.

Figure 14:
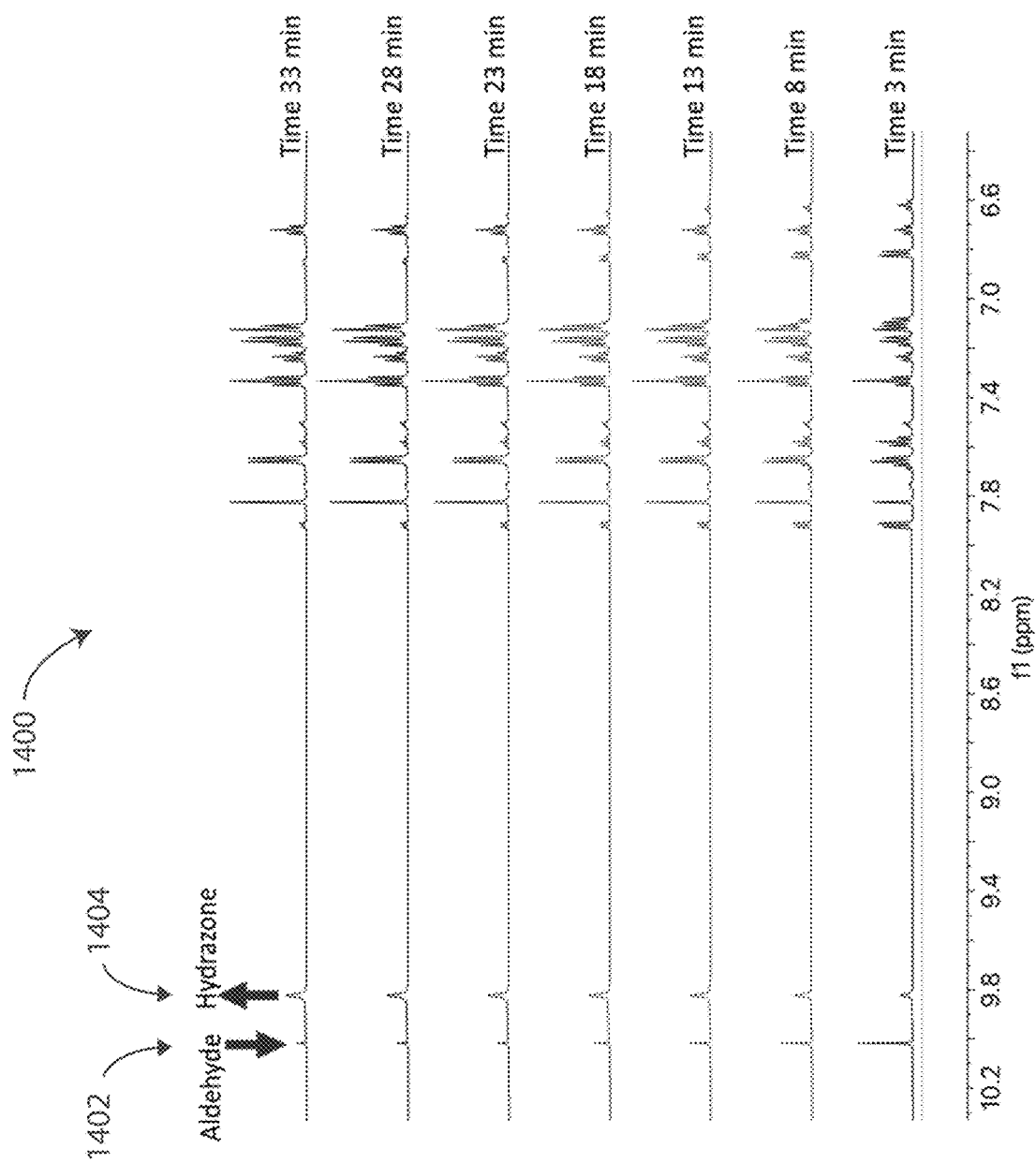
FIG. 14 is a series of $^1$H NMR spectra of exemplary reaction in accordance with various embodiments herein.

As shown in FIG. 14, the HCO peak 1402 of benzaldehyde at 10.2 ppm declines over the span of 35 minutes when a 1.4:1 ratio (molar equivalents) of the reactants phenylhydrazine to benzaldehyde was used. At the same time, the HCN peak 1404 at 9.8 ppm corresponding to the hydrazone product increases over time shows an increase over the span of 35 minutes when a 1.4:1 ratio (molar equivalents) of the reactants phenylhydrazine to benzaldehyde was used. The ¹H NMR data reveal that a 1.4:1 molar ratio of phenylhydrazine to benzaldehyde in this reaction favors the formation of the hydrazone product. The decline of benzaldehyde from 3 minutes (bottom) to 33 minutes (top) indicates the conversion of the reactants into the hydrazone product. A mixture of E and Z isomers was observed in the hydrazone reaction product.

Figure 15:
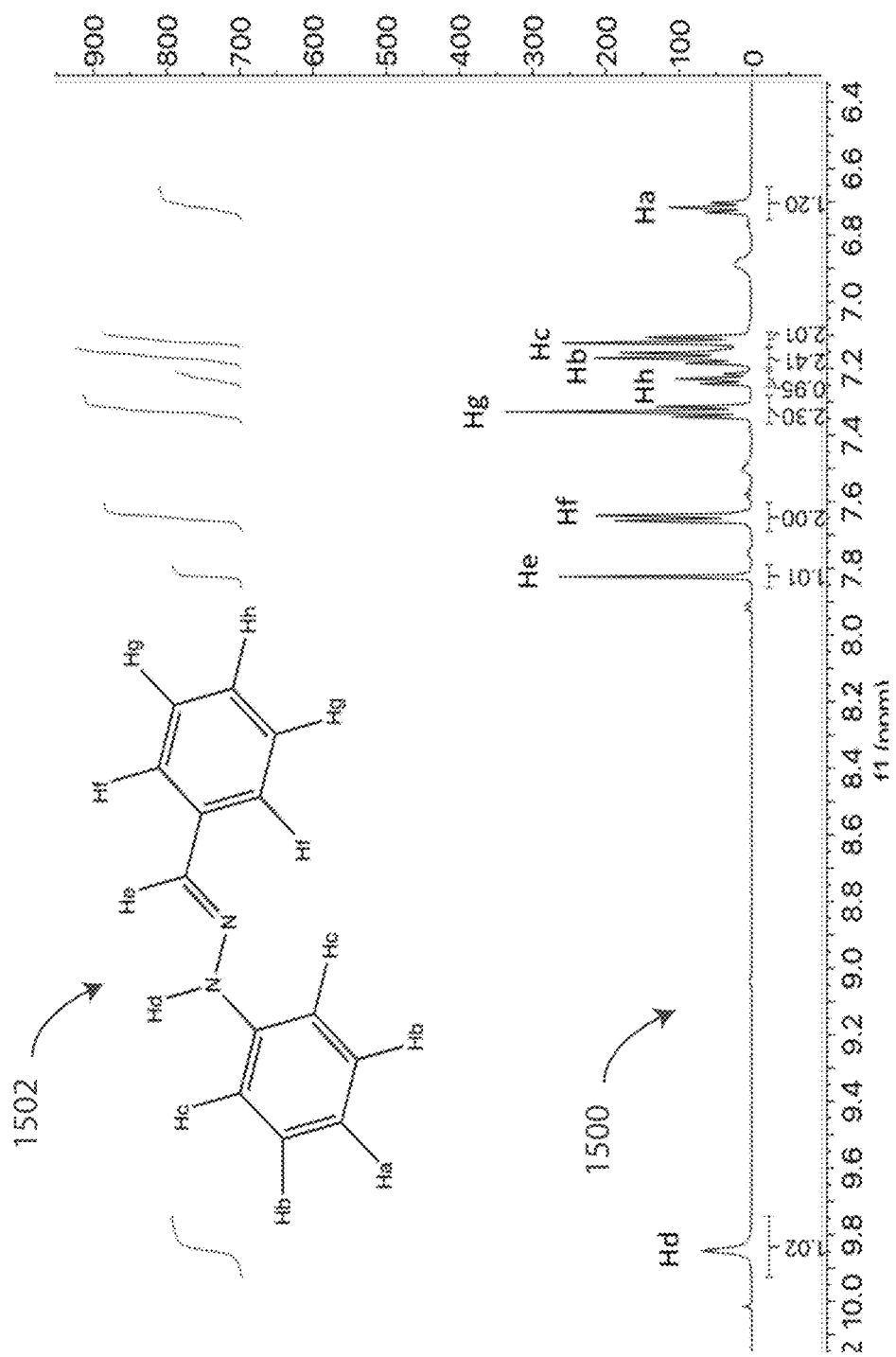
FIG. 15 is a representative $^1$H NMR spectrum of exemplary compound in accordance with various embodiments herein.

A ¹H NMR spectrum 1500 with various hydrazone product peaks labelled is shown in FIG. 15. The ¹H NMR spectrum (500 MHz) of the phenylhydrazine/benzaldehyde (1.4:1 molar equivalents) reaction (THF-d$_8$, 5% v/v H$_2$O, 5 mol % THF) of FIG. 14 was obtained at 20 minutes. Peak labeled H$_a$, H$_b$, H$_c$, H$_d$, H$_e$, H$_f$, H$_g$, and h$_h$ correspond to the hydrazone product structure (inlay 1502).

Example 7: Determination of Initial Rate Constants

To determine the reaction kinetics of O-phenylhydroxylamine and phenylhydrazine with benzaldehyde, each reaction was monitored by ¹H NMR spectroscopy. The integration of each peak was plotted over time. Using second order reaction kinetics, a model was developed and the time and concentration data for both the probe and aldehyde were fit simultaneously to determine the initial rate constant of the reaction (k$_o$).

Figure 16:
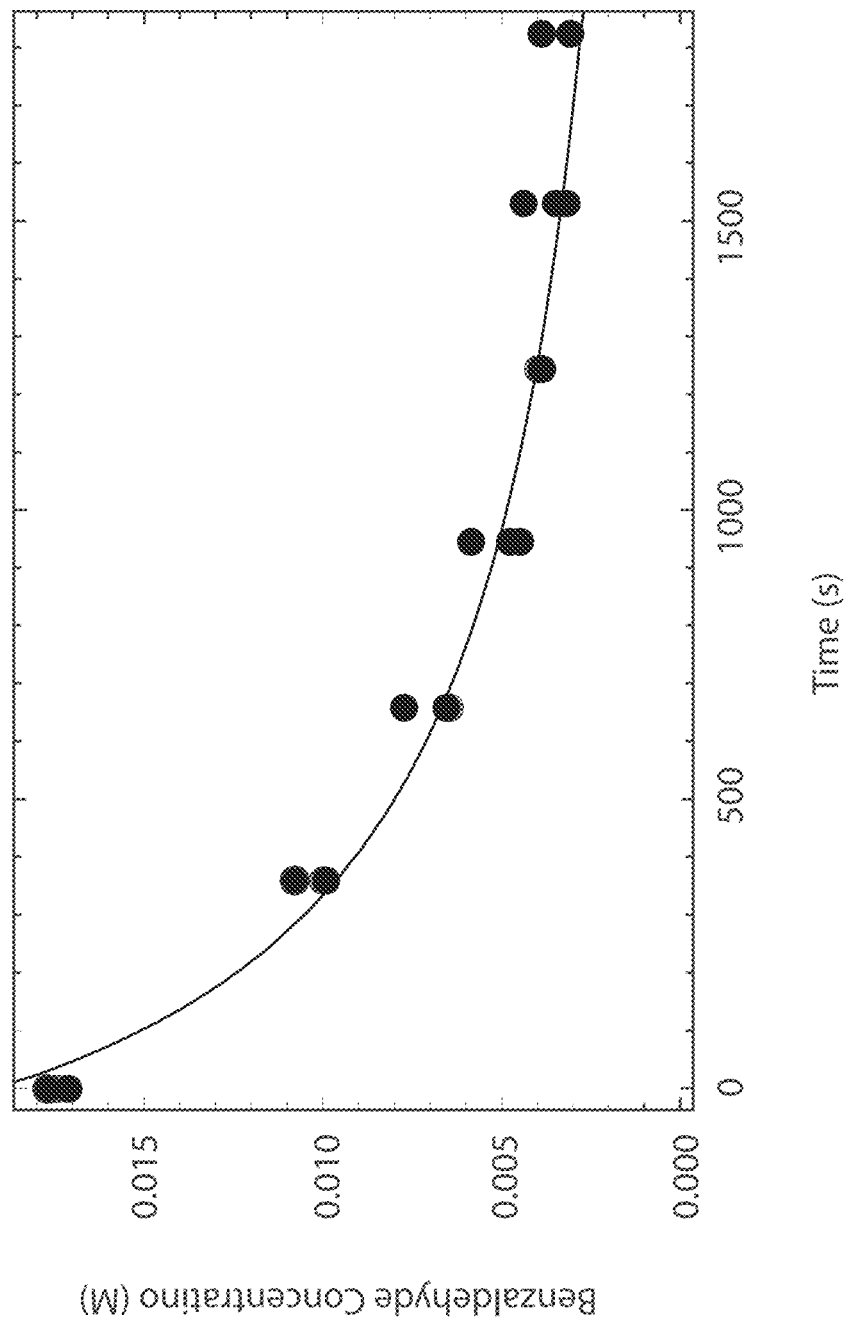
FIG. 16 is a representative plot of concentration of reactant with respect to time for an exemplary reaction in accordance with various embodiments herein.
Figure 17:
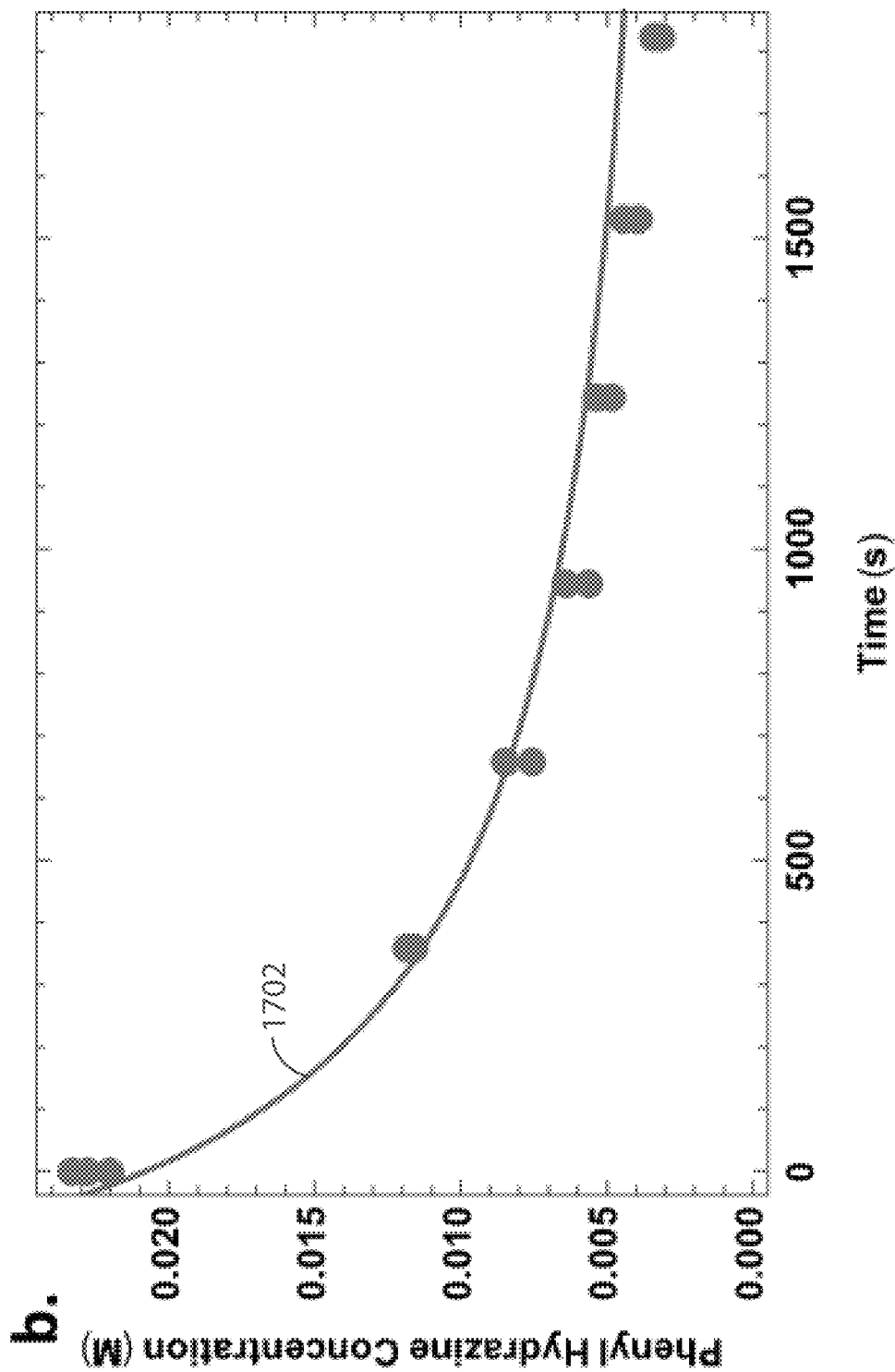
FIG. 17 is a representative plot of concentration of reactant with respect to time for an exemplary reaction in accordance with various embodiments herein.

Referring now to FIGS. 16 and 17, representative plots of the concentration of reactant with respect to time for benzaldehyde (FIG. 16) and phenylhydrazine (FIG. 17). Line 1602 of FIG. 17 and line 1702 of FIG. 17 represents the model fit to give the initial rate constant (k$_o$) for each reaction. The model was developed using math software and was used to relate the time to the concentration of each species with k$_o$ as a variable. The values of constants in the equation were determined using the initial concentrations of the reaction species and the data was fit to these to determine the mean k$_o$ for each probe of interest (Table 1).

TABLE 1

Initial rate constants, k$_o$, and the relative standard deviations determined from ¹H NMR data for the reaction of O-phenylhydroxylamine or phenylhydrazine with benzaldehyde.

| Probe | k$_o$ (L · mol⁻¹ · s⁻¹) | Standard Deviation |
|---|---|---|
| O-phenylhydroxylamine | 0.0062 | 0.0002 |
| phenylhydrazine | 0.128 | 0.006 |

The results show that the reaction of phenylhydrazine with benzaldehyde is faster than the reaction of O-phenylhydroxylamine with benzaldehyde, showing further that the equilibrium favors the formation of the hydrazone product in the reaction of phenylhydrazine with benzaldehyde.

Example 8: Synthesis of 4-hexadecylphenylhydrazine

The synthesis of the sensing probe 4-hexadecylphenylhydrazine, was performed according to the following reaction scheme:

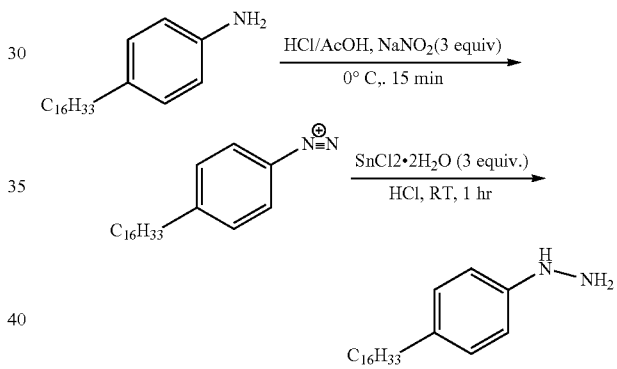

The synthesis was performed as follows: To a cooled round bottom flask of concentrated hydrochloric acid (3 mL) and acetic acid (9 mL), 4-hexadecylaniline (1 mmol, 0.32 g) was added. The suspension was stirred vigorously at 0° C. for 30 min, followed by a dropwise addition of an aqueous solution of NaNO$_2$ (1.8 mmol, 0.12 g. in deionized water, 1 mL) over 5 minutes. After stirring at 0° C. for an additional 15 min, the reaction mixture was added dropwise into a stirred room-temperature solution of tin (II) chloride dihydrate (SnCl$_2$·H$_2$O, 3 mmol, 0.7 g) in 5 mL of concentrated hydrochloric acid, resulting in the formation of a white precipitate. After stirring for 1 h, the white precipitate was collected through vacuum filtration and rinsed with deionized water. The collected product was then suspended in 2M NaOH (10 mL) and again filtered and rinsed with deionized water to yield a light orange crude product, which was dried under vacuum.

Example 9: Purification of 4-hexadecylphenylhydrazine

The light orange crude 4-hexadeylphenylhydrazine was dissolved in tetrahydrofuran (THF) and cooled to 0° C. while adding concentrated HCl dropwise to result in the precipitation of a white hydrochloride salt. The white hydrochloride salt was filtered, rinsed with THF to remove any residual side products, and rinsed three times with 5% NaOH solution to neutralize. The resulting white solid was dried under vacuum, and the precipitation was repeated, as necessary, to achieve an analytically pure product having the following $^1$H NMR (500 MHz, THF-d$_8$, δ) profile: 9.46 (s, 1H), 6.93 (d, 2H, J=6.94 Hz), 6.72 (d, 2H, J=6.71 Hz), 5.82 (s, 2H), 1.32 (s, 30H), 0.92 (t, 3H, J=0.92 Hz). ESI-MS 333.4 m/z.

Example 10: Graphene Modification with 4-hexadecylphenylhydrazine

Figure 18:
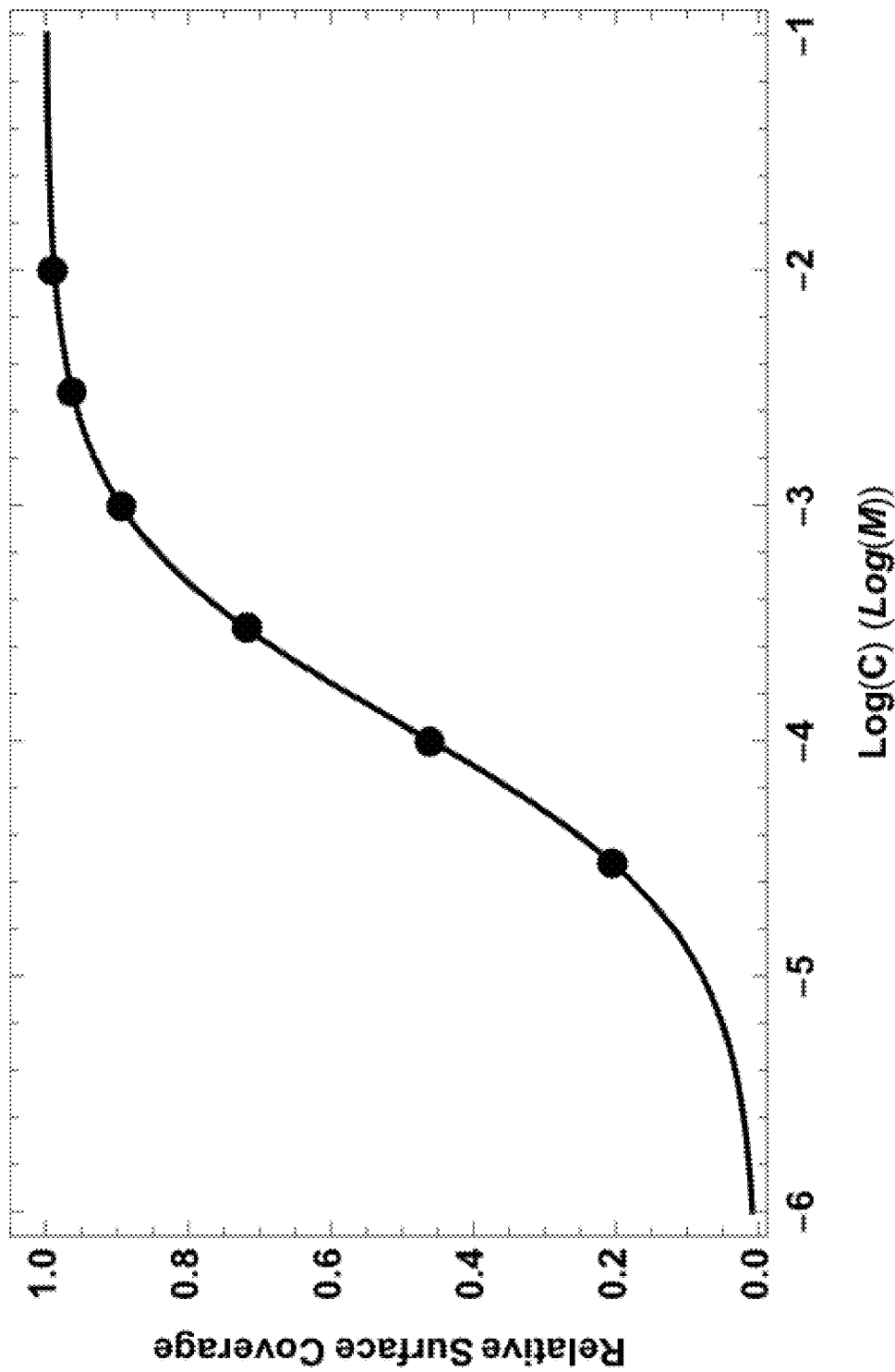
FIG. 18 is a representative plot of relative surface coverage as a function of the logarithm of concentration in accordance with various embodiments herein.

Contact angle measurements of graphene modified with 4-hexadeylphenylhydrazine was performed with a contact angle goniometer (Erma, Tokyo, Japan). A drop of 4 microliters (μl), 8 μl or 12 μl of an appropriate solvent, as described elsewhere herein, was placed onto the graphene surface, and the average contact angle was obtained from 6 advancing contact angle readings at two spots. The logarithm of the concentration as a function of relative surface coverage for the adsorption of 4-hexadeylphenylhydrazine to graphene is shown in FIG. 18. The relative surface coverage (θ) as determined by contact angle goniometry for graphene modified with 4-hexadeylphenylhydrazine is, θ (sat)=76.6°±0.2° (K=8548±500 M$^{-1}$; Log(K)=3.93 Log (M$^{-1}$)).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device comprising:
a graphene varactor comprising:
a graphene layer;
a self-assembled monolayer disposed on an outer surface of the graphene layer through electrostatic interactions between a partial positive charge on hydrogen atoms of one or more hydrocarbons of the self-assembled monolayer and π-electron system of graphene; and
wherein the self-assembled monolayer comprises one or more compounds comprising one or more hydrazine groups or hydroxylamine groups, substituted hydrazine or hydroxylamine groups, or derivatives thereof.

2. The medical device of claim 1, wherein the self-assembled monolayer provides a Langmuir theta value of at least 0.9.

3. The medical device of claim 1, wherein the self-assembled monolayer provides coverage over the graphene from 50% to 150% by surface area.

4. The medical device of claim 1, wherein the self-assembled monolayer further includes an acidic compound effective to catalyze a reaction between the hydrazine groups or hydroxylamine groups and an aldehyde or ketone.

5. The medical device of claim 1, the self-assembled monolayer comprising compounds of a formula:

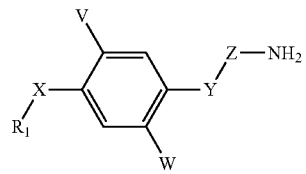

wherein Z comprises NH or O;
wherein R$^1$ comprises (CH$_2$)$_m$CH$_3$, wherein 50>m>5;
wherein X comprises CH$_2$, O, NH, N(CH$_2$)$_n$CH$_3$, —C(=O)O—, —OC(=O)—, —C(=O)NH—, —NHC(=O)—, —C(=O)N((CH$_2$)$_n$CH$_3$)—, —N((CH$_2$)$_n$CH$_3$)C(=O)—, —S—, —S(=O)—, —S(=O)$_2$—, —S(=O)$_2$O—, —OS(=O)$_2$—, —S(=O)$_2$NH—, —NHS(=O)$_2$—, —S(=O)$_2$N((CH$_2$)$_n$CH$_3$)—, —N((CH$_2$)$_n$CH$_3$)S(=O)$_2$—, and wherein n is 0, or 1 to 20;
wherein Y comprises (C$_6$H$_4$)$_p$ or (CH$_2$)$_p$, wherein p is 0, 1, or 2;
wherein W comprises H, (CH$_2$)$_q$OH, (CH$_2$)$_q$COOH, (CH$_2$)$_q$SO$_2$OH, or (CH$_2$)$_q$PO$_2$OH, wherein q is 0, 1, or 2;
wherein V comprises H, NO, NO$_2$, Cl, Br, I, F, CF$_3$, —CN, —NC, C$_6$H$_5$ (phenyl), OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$^2$S(=O)$_2$R, wherein R and R$^2$ comprise (CH$_2$)$_k$CH$_3$ and k is 0, 1, or 2;
wherein R$^1$X and V can be present in any ring position relative to a YZNH$_2$ group and W is present in an alpha position relative to the YZNH$_2$ to provide proximity between W and YZNH$_2$; and any tautomers thereof.

6. The medical device of claim 5, wherein W is present in the alpha position effective to permit interaction of an acidic hydrogen atom on W with an aldehyde molecule so as to catalyze a reaction of the aldehyde with the hydrazine group or hydroxylamine group.

7. The medical device of claim 5, wherein the formula comprises more than one R$^1$X moiety effective to induce self-assembly of the compound.

8. The medical device of claim 5, wherein the formula comprises more than one V moiety effective to provide electron density to the compound.

9. The medical device of claim 1, the self-assembled monolayer comprising compounds of the formula:

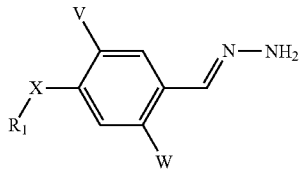

wherein R$^1$ comprises (CH$_2$)$_m$CH$_3$, wherein 50>m>5;
wherein X comprises CH$_2$, O, NH, N(CH$_2$)$_n$CH$_3$, —C(=O)O—, —OC(=O)—, —C(=O)NH—, —NHC(=O)—, —C(=O)N((CH$_2$)$_n$CH$_3$)—, —N((CH$_2$)$_n$CH$_3$)C(=O)—, —S—, —S(=O)—, —S(=O)$_2$—, —S(=O)$_2$O—, —OS(=O)$_2$—, —S(=O)$_2$NH—, —NHS(=O)$_2$—, —S(=O)$_2$N((CH$_2$)$_n$CH$_3$)—, —N((CH$_2$)$_n$CH$_3$)S(=O)$_2$— and wherein n is 0, or 1 to 20;
wherein W comprises H, (CH$_2$)$_q$OH, (CH$_2$)$_q$COOH, (CH$_2$)$_q$SO$_2$OH, or (CH$_2$)$_q$PO$_2$OH, wherein q is 0, 1, or 2;
wherein V comprises H, NO, NO$_2$, Cl, Br, I, F, CF$_3$, —CN, —NC, C$_6$H$_5$ (phenyl), OR, —C(=O)R, SR, COOR, OCOOR, —S(=O)R, —S(=O)$_2$R, —S(=O)$_2$OR, —OS(=O)$_2$R, —S(=O)$_2$NHR, —NHS(=O)$_2$R, —S(=O)$_2$NRR$^2$, —NR$^2$S(=O)$_2$R, wherein R and R$^2$ comprise (CH$_2$)$_k$CH$_3$ and k is 0, 1, or 2;
wherein R$^1$X and V can be present in any ring position relative to an NNH$_2$ group and W is present in an alpha position relative to the NNH$_2$ group; and
any tautomers thereof.

10. The medical device of claim 9, wherein W is present in the alpha position effective to permit interaction of an acidic hydrogen atom on W with an aldehyde molecule so as to catalyze a reaction of the aldehyde with the hydrazine group or hydroxylamine group.

11. The medical device of claim 1, the self-assembled monolayer comprising compounds of the formula:

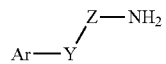

wherein Z comprises NH or O;
where Y comprises (CH$_2$)$_p$, wherein p is from 0 to 20;
wherein Ar comprises an aromatic substituent with 16 or more aromatic carbons; and
any tautomers thereof.

12. The medical device of claim 11, wherein the aromatic substituent comprises naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof.

13. The medical device of claim 11, wherein the aromatic substituent further comprises one or more substitutions including (CH$_2$)$_q$OH, (CH$_2$)$_q$COOH, (CH$_2$)$_q$SO$_2$OH, or (CH$_2$)$_q$PO$_2$OH, in a position alpha to a YZNH$_2$ group effective to permit interaction of an acidic hydrogen atom on the substitution with an aldehyde molecule so as to catalyze a reaction of the aldehyde with the hydrazine or hydroxylamine group.

14. The medical device of claim 1, the self-assembled monolayer comprising compounds of the formula:

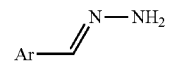

wherein Ar comprises an aromatic substituent with 16 or more aromatic carbons; and
any tautomers thereof.

15. The medical device of claim 14, wherein the aromatic substituent comprises naphthacene, benzanthracene, chrysene, pentacene, dibenzanthracene, triphenylene, pyrene, benzopyrene, picene, perylene, benzoperylene, pentaphene, pentacene, anthanthrene, coronene, ovalene, or derivatives thereof.

16. The medical device of claim 14, wherein the aromatic substituent further comprises one or more substitutions including (CH$_2$)$_q$OH, (CH$_2$)$_q$COOH, (CH$_2$)$_q$SO$_2$OH, or (CH$_2$)$_q$PO$_2$OH, in a position alpha to a NNH$_2$ group effective to permit interaction of an acidic hydrogen atom on the substitution with an aldehyde molecule.

17. A method of modifying a surface of graphene to create a graphene varactor, the method comprising:
forming a self-assembled monolayer disposed on an outer surface of the graphene layer through electrostatic interactions between a partial positive charge on hydrogen atoms of more hydrocarbons of the self-assembled monolayer and a π-electron system of graphene;
the self-assembled monolayer comprising one or more compounds comprising hydrazine or hydroxylamine groups, substituted hydrazine or hydroxylamine groups, or derivatives thereof.

18. The method of claim 17, further comprising quantifying an extent of surface coverage of the self-assembled monolayer using contact angle goniometry, Raman spectroscopy, or x-ray photoelectron spectroscopy.

19. A method for detecting an analyte comprising:
collecting a gaseous sample from a patient;
contacting the gaseous sample with one or more graphene varactors, each of the one or more graphene varactors comprising
a graphene layer;
a self-assembled monolayer disposed on an outer surface of the graphene layer through electrostatic interactions between a partial positive charge on hydrogen atoms of more hydrocarbons of the self-assembled monolayer and a π-electron system of graphene; and
wherein the self-assembled monolayer comprises at least one selected from the group consisting of compounds comprising hydrazine or hydroxylamine groups, substituted hydrazine or hydroxylamine groups, or derivatives thereof.

20. The method of claim 19, further comprising measuring a differential response in an electrical property of the one or more graphene varactors due to binding of one or more analytes present in the gaseous sample.

* * * * *